US009645131B1

(12) United States Patent
Deslauriers et al.

(10) Patent No.: US 9,645,131 B1
(45) Date of Patent: May 9, 2017

(54) POLYMER COMPOSITIONS HAVING IMPROVED PROCESSABILITY AND METHODS OF MAKING AND USING SAME

(71) Applicant: Chevron Phillips Chemical Company LP, The Woodlands, TX (US)

(72) Inventors: Paul J. Deslauriers, Owasso, OK (US); Jerry Stark, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 14/960,056

(22) Filed: Dec. 4, 2015

(51) Int. Cl.
*C08F 10/02* (2006.01)
*G01N 33/44* (2006.01)
*C08J 5/18* (2006.01)
*C08F 110/02* (2006.01)
*G01N 5/00* (2006.01)

(52) U.S. Cl.
CPC .......... *G01N 33/442* (2013.01); *C08F 110/02* (2013.01); *C08J 5/18* (2013.01); *G01N 5/00* (2013.01); *C08F 2500/05* (2013.01); *C08F 2500/24* (2013.01); *C08F 2500/26* (2013.01); *C08J 2323/06* (2013.01)

(58) Field of Classification Search
CPC ....... C08L 23/06; C08L 2203/16; C08F 10/02
See application file for complete search history.

(56) References Cited

U.S. PATENT DOCUMENTS

| | | |
|---|---|---|
| 3,248,179 A | 4/1966 | Norwood |
| 4,461,873 A * | 7/1984 | Bailey .............. C08L 23/06 525/240 |
| 4,501,885 A | 2/1985 | Sherk et al. |
| 4,540,538 A | 9/1985 | Corwin et al. |
| 4,588,790 A | 5/1986 | Jenkins, III et al. |
| 4,939,217 A | 7/1990 | Stricklen |
| 5,191,132 A | 3/1993 | Patsidis et al. |
| 5,210,352 A | 5/1993 | Alt et al. |
| 5,347,026 A | 9/1994 | Patsidis et al. |
| 5,352,749 A | 10/1994 | DeChellis et al. |
| 5,399,636 A | 3/1995 | Alt et al. |
| 5,401,817 A | 3/1995 | Palackal et al. |
| 5,409,646 A | 4/1995 | Menon et al. |
| 5,420,320 A | 5/1995 | Zenk et al. |
| 5,436,304 A | 7/1995 | Griffin et al. |
| 5,436,305 A | 7/1995 | Alt et al. |
| 5,451,649 A | 9/1995 | Zenk et al. |
| 5,455,314 A | 10/1995 | Burns et al. |
| 5,496,781 A | 3/1996 | Geerts et al. |
| 5,498,581 A | 3/1996 | Welch et al. |
| 5,541,272 A | 7/1996 | Schmid et al. |
| 5,554,795 A | 9/1996 | Frey et al. |
| 5,563,284 A | 10/1996 | Frey et al. |
| 5,565,175 A | 10/1996 | Hottovy et al. |
| 5,565,592 A | 10/1996 | Patsidis et al. |
| 5,571,880 A | 11/1996 | Alt et al. |
| 5,575,979 A | 11/1996 | Hanson |
| 5,594,078 A | 1/1997 | Welch et al. |
| 5,631,203 A | 5/1997 | Welch et al. |
| 5,631,335 A | 5/1997 | Alt et al. |
| 5,654,454 A | 8/1997 | Peifer et al. |
| 5,668,230 A | 9/1997 | Schertl et al. |
| 5,705,579 A | 1/1998 | Hawley et al. |
| 6,031,027 A | 2/2000 | Syre et al. |
| 6,114,486 A | 9/2000 | Rowland et al. |
| 6,187,880 B1 | 2/2001 | Welch et al. |
| 6,239,235 B1 | 5/2001 | Hottovy et al. |
| 6,262,191 B1 | 7/2001 | Hottovy et al. |
| 6,299,342 B2 | 10/2001 | Eggen et al. |
| 6,416,663 B1 | 7/2002 | Miroslav et al. |
| 6,509,427 B1 | 1/2003 | Welch et al. |
| 6,573,343 B1 | 6/2003 | Follestad |
| 6,833,415 B2 | 12/2004 | Kendrick et al. |

(Continued)

FOREIGN PATENT DOCUMENTS

| | | |
|---|---|---|
| CN | 103217360 A | 7/2013 |
| WO | 9511264 A1 | 4/1995 |
| WO | 2013037498 A1 | 3/2013 |

OTHER PUBLICATIONS

Alt, Helmut G., et al., "C1-Bridged fluorenylidene cyclopentadienylidene complexes of the type (C13H8-CR1R2-C5H3R)ZrCl2 (R1, R2=alkyl, phenyl, alkenyl; R=H, alkyl, alkenyl, substituted silyl) as catalyst precursors for the polymerization of ethylene and propylene," Journal of Organometallic Chemistry, 1998, pp. 87-112, vol. 568, Elsevier Science S.A.

Alt, Helmut G., et al., "C1-verbrückte Fluorenyliden—Indenylidenkomplexe des Typs (C13H8-CR2-C9H6_nR'n) ZrCl2 (n=0, 1; R=Me, Ph, Butenyl; R'=Alkyl, Alkenyl) als Metallocenkatalysatorvorstufen für die Ethylenpolymerisation," Journal of Organometallic Chemistry, 1998, pp. 153-181, vol. 562, Elsevier Science S.A.

Cardin, D. J., et al., "Chemistry of Organo-Zirconium and -Hafnium Compounds," 1986, 5 pages of cover, publishing information, and contents, Halstead Press: a division of John Wiley & Sons, New York.

Filing receipt and specification for patent application entitled "Polymer Compositions Having Improved Processability and Methods of Making and Using Same," by Youlu Yu, et al., filed Dec. 4, 2015 as U.S. Appl. No. 14/960,047.

(Continued)

*Primary Examiner* — Rip A Lee

(74) *Attorney, Agent, or Firm* — Conley Rose, P.C.; Rodney B. Carroll; Chad Walter

(57) ABSTRACT

A method of preparing a polymer article comprising preparing a plurality of polymer samples having a lower molecular weight (LMW) component and a higher molecular weight (HMW) component; sieving each of the plurality polymer samples to produce a corresponding plurality of sieved polymer samples; determining a heterogeneity value for each of the plurality of polymer samples; identifying at least one polymer sample from the plurality of polymer samples having a predicted gel count of less than 100 gels/ft² wherein the predicted gel count is a function of the heterogeneity value; and fabricating a film from the identified polymer sample having a predicted gel count of less than about 100 gels/ft².

24 Claims, 7 Drawing Sheets

(56) References Cited

U.S. PATENT DOCUMENTS

| | | |
|---|---|---|
| 6,855,654 B2 | 2/2005 | Kissin et al. |
| 6,878,454 B1 | 4/2005 | Shannon et al. |
| 6,900,266 B2 | 5/2005 | Raty |
| 7,026,494 B1 | 4/2006 | Yang et al. |
| 8,188,170 B2 | 5/2012 | Zahalka et al. |
| 8,445,599 B2 | 5/2013 | Gustafsson et al. |
| 2005/0127559 A1 | 6/2005 | Eggen et al. |
| 2009/0252910 A1 | 10/2009 | Baeckman et al. |
| 2010/0190926 A1 | 7/2010 | Krishnaswamy et al. |
| 2012/0059134 A1 | 3/2012 | Yang et al. |
| 2012/0205832 A1 | 8/2012 | Rahim et al. |
| 2013/0096266 A1 | 4/2013 | Van Dun et al. |
| 2013/0099424 A1 | 4/2013 | Rohatgi et al. |
| 2013/0338314 A1 | 12/2013 | Dewachter et al. |

OTHER PUBLICATIONS

Kajigaeshi, Shoji, et al., "Selective Preparation of Fluorene Derivatives Using the t-Butyl Function as a Positional Protective Group," Bull. Chem. Soc. Jpn., Jan. 1986, pp. 97-103, vol. 59, No. 1, The Chemical Society of Japan.

Köppl, Alexander, et al., "Heterogeneous metallocene catalysts for ethlene polymerization," Journal of Molecular Catalysis A: Chemical, 2001, pp. 23-32, vol. 165, Elsevier Science B.V.

Rauwendaal, Chris, "What's Causing Your Gels?" Plastics Technology, http://www.ptonline.com/articles/what's-causing-your-gels, Mar. 2002, 4 pages, Gardner Business Media, Inc.

Wailes, P. C., et al., "Organometallic Chemistry of Titanium, Zirconium, and Hafnium," 1974, 6 pages of cover, publishing information, and contents, Academic Press, New York.

Office Action dated Sep. 14, 2016 (18 pages), U.S. Appl. No. 14/960,047, filed Dec. 4, 2015.

Foreign communication from a related counterpart application—International Search Report, PCT/US2016/064321, Mar. 2, 2017, 4 pages.

Foreign communication from a related counterpart application—International Search Report, PCT/US2016/063986, Mar. 7, 2017, 5 pages.

* cited by examiner

POLYMER COMPOSITIONS HAVING IMPROVED PROCESSABILITY AND METHODS OF MAKING AND USING SAME

TECHNICAL FIELD

The present disclosure relates to polymer compositions having improved processability. More particularly, the present disclosure relates to the preparation of polymer articles having reduced defects.

BACKGROUND

Polyolefins are plastic materials useful for making a wide variety of valued products due to their combination of features such as stiffness, ductility, barrier properties, temperature resistance, optical properties, availability, and low cost. In particular, polyethylene (PE) is one of the largest volume polymers consumed in the world. It is a versatile polymer that offers high performance relative to other polymers and alternative materials such as glass or metal. One of the most valued polyolefin products is plastic film. An ongoing need exists for improved polymer compositions displaying desired processing characteristics for producing articles such as film.

SUMMARY

Disclosed herein is a method of preparing a polymer article comprising preparing a plurality of polymer samples having a lower molecular weight (LMW) component and a higher molecular weight (HMW) component; sieving each of the plurality polymer samples to produce a corresponding plurality of sieved polymer samples; determining a heterogeneity value for each of the plurality of polymer samples; identifying at least one polymer sample from the plurality of polymer samples having a predicted gel count of less than 100 gels/ft$^2$ wherein the predicted gel count is a function of the heterogeneity value; and fabricating a film from the identified polymer sample having a predicted gel count of less than about 100 gels/ft$^2$.

Also disclosed herein is a method of preparing a polymer article comprising preparing a polymer sample having a lower molecular weight (LMW) component and a higher molecular weight (HMW) component; separating the polymer sample to produce a plurality of polymer sample subpopulations based on particle size; determining a weight fraction for each of the plurality of polymer sample subpopulations based on a total weight of the polymer sample; and determining a heterogeneity ($\Psi$) value of the polymer sample based on a molecular weight distribution for the polymer sample subpopulations wherein a polymer sample having a heterogeneity value of greater than about 3 is designated a high gel forming polymer (HGFP).

Also disclosed herein is a method of preparing a polymer article comprising preparing a polymer sample having a lower molecular weight (LMW) component and a higher molecular weight (HMW) component; sieving the polymer sample to produce a plurality of sieved polymer samples; determining the heterogeneity value for each one of the plurality of sieved polymer samples; identifying at least one sieved polymer sample having a predicted gel count of less than about 100 gels/ft$^2$ wherein the predicted gel count is a function of the heterogeneity value; and fabricating an article from one or more of the sieved polymer samples having a predicted gel count of less than about 100 gels/ft$^2$.

DETAILED DESCRIPTION

Figure 1:
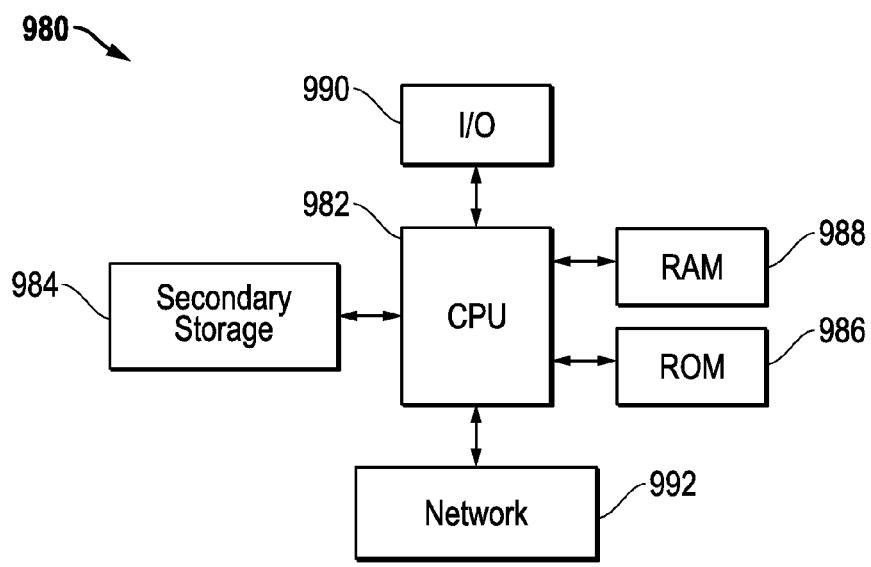
FIG. 1 is an embodiment of a computer system for implementation of methodologies of the type disclosed herein.

Disclosed herein are polymer compositions having improved processability and methods of identifying, making, and using same. Herein a metric of improved processability is the extent of gel formation in a polymer article. Herein gels refer to visual defects that result due to the presence of discrete bodies that are not sufficiently interspersed with the bulk material and reflect and transmit light differently from the rest of the material. As utilized herein, gels are further defined as particles greater than 200 micron in size. Gels may be formed during the polymerization process and in such cases are termed P-gels. Alternatively the gels may form during extrusion of the polymer and are termed E-gels. Disclosed herein are methodologies for determining the propensity of polymer compositions to form gels when fabricated into an article. In an embodiment, the gels are E-gels.

In an embodiment, a method of the present disclosure comprises preparing a polymer composition. In an embodiment, a polymer composition of the type described herein may be prepared by any suitable methodology, for example by employing one or more catalyst systems, in one or more reactors, in solution, in slurry, or in the gas phase, and/or by varying the monomer concentration in the polymerization reaction, and/or by changing any/all of the materials or parameters involved in the production of the polymer compositions, as will be described in more detail later herein.

The polymer composition of the present disclosure can be produced using various types of polymerization reactors. As used herein, "polymerization reactor" includes any reactor capable of polymerizing olefin monomers to produce homopolymers and/or copolymers. Homopolymers and/or copolymers produced in the reactor may be referred to as resin and/or polymers. The various types of reactors include, but are not limited to those that may be referred to as batch, slurry, gas-phase, solution, high pressure, tubular, autoclave, or other reactor and/or reactors. Gas phase reactors may comprise fluidized bed reactors or staged horizontal reactors. Slurry reactors may comprise vertical and/or horizontal loops. High pressure reactors may comprise autoclave and/or tubular reactors. Reactor types may include batch and/or continuous processes. Continuous processes may use intermittent and/or continuous product discharge or transfer. Processes may also include partial or full direct recycle of un-reacted monomer, un-reacted comonomer, catalyst and/or co-catalysts, diluents, and/or other materials of the polymerization process.

Polymerization reactor systems of the present disclosure may comprise one type of reactor in a system or multiple reactors of the same or different type, operated in any suitable configuration. Production of polymers in multiple reactors may include several stages in at least two separate polymerization reactors interconnected by a transfer system making it possible to transfer the polymers resulting from the first polymerization reactor into the second reactor. Alternatively, polymerization in multiple reactors may include the transfer, either manual or automatic, of polymer from one reactor to subsequent reactor or reactors for additional polymerization. Alternatively, multi-stage or multi-step polymerization may take place in a single reactor, wherein the conditions are changed such that a different polymerization reaction takes place.

The desired polymerization conditions in one of the reactors may be the same as or different from the operating conditions of any other reactors involved in the overall process of producing the polymer of the present disclosure. Multiple reactor systems may include any combination including, but not limited to multiple loop reactors, multiple gas phase reactors, a combination of loop and gas phase reactors, multiple high pressure reactors or a combination of high pressure with loop and/or gas reactors. The multiple reactors may be operated in series or in parallel. In an embodiment, any arrangement and/or any combination of reactors may be employed to produce the polymer of the present disclosure.

According to one embodiment, the polymerization reactor system may comprise at least one loop slurry reactor. Such reactors may comprise vertical or horizontal loops. Monomer, diluent, catalyst system, and optionally any comonomer may be continuously fed to a loop slurry reactor, where polymerization occurs. Generally, continuous processes may comprise the continuous introduction of a monomer, a catalyst, and/or a diluent into a polymerization reactor and the continuous removal from this reactor of a suspension comprising polymer particles and the diluent. Reactor effluent may be flashed to remove the liquids that comprise the diluent from the solid polymer, monomer and/or comonomer. Various technologies may be used for this separation step including but not limited to, flashing that may include any combination of heat addition and pressure reduction; separation by cyclonic action in either a cyclone or hydrocyclone; separation by centrifugation; or other appropriate method of separation.

Typical slurry polymerization processes (also known as particle-form processes) are disclosed in U.S. Pat. Nos. 3,248,179, 4,501,885, 5,565,175, 5,575,979, 6,239,235, 6,262,191 and 6,833,415, for example; each of which are herein incorporated by reference in their entirety.

Suitable diluents used in slurry polymerization include, but are not limited to, the monomer being polymerized and hydrocarbons that are liquids under reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used. An example is polymerization of propylene monomer as disclosed in U.S. Pat. No. 5,455,314, which is incorporated by reference herein in its entirety.

According to yet another embodiment, the polymerization reactor may comprise at least one gas phase reactor. Such systems may employ a continuous recycle stream containing one or more monomers continuously cycled through a fluidized bed in the presence of the catalyst under polymerization conditions. A recycle stream may be withdrawn from the fluidized bed and recycled back into the reactor. Simultaneously, polymer product may be withdrawn from the reactor and new or fresh monomer may be added to replace the polymerized monomer. Such gas phase reactors may comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 4,588,790, 5,352,749, and 5,436,304, each of which is incorporated by reference in its entirety herein.

According to still another embodiment, a high pressure polymerization reactor may comprise a tubular reactor or an autoclave reactor. Tubular reactors may have several zones where fresh monomer, initiators, or catalysts are added. Monomer may be entrained in an inert gaseous stream and introduced at one zone of the reactor. Initiators, catalysts, and/or catalyst components may be entrained in a gaseous stream and introduced at another zone of the reactor. The gas streams may be intermixed for polymerization. Heat and pressure may be employed appropriately to obtain optimal polymerization reaction conditions.

According to yet another embodiment, the polymerization reactor may comprise a solution polymerization reactor wherein the monomer is contacted with the catalyst composition by suitable stirring or other means. A carrier comprising an organic diluent or excess monomer may be employed. If desired, the monomer may be brought in the vapor phase into contact with the catalytic reaction product, in the presence or absence of liquid material. The polymerization zone is maintained at temperatures and pressures that will result in the formation of a solution of the polymer in a reaction medium. Agitation may be employed to obtain better temperature control and to maintain uniform polymerization mixtures throughout the polymerization zone. Adequate means are utilized for dissipating the exothermic heat of polymerization.

Polymerization reactors suitable for the present disclosure may further comprise any combination of at least one raw material feed system, at least one feed system for catalyst or catalyst components, and/or at least one polymer recovery system. Suitable reactor systems for the present invention may further comprise systems for feedstock purification, catalyst storage and preparation, extrusion, reactor cooling, polymer recovery, fractionation, recycle, storage, loadout, laboratory analysis, and process control.

Conditions that are controlled for polymerization efficiency and to provide polymer properties include, but are not limited to temperature, pressure, type and quantity of catalyst or co-catalyst, and the concentrations of various reactants. Polymerization temperature can affect catalyst productivity, polymer molecular weight and molecular weight distribution. Suitable polymerization temperatures may be any temperature below the de-polymerization temperature, according to the Gibbs Free Energy Equation. Typically, this includes from about 60° C. to about 280° C., for example, and/or from about 70° C. to about 110° C., depending upon the type of polymerization reactor and/or polymerization process.

Suitable pressures will also vary according to the reactor and polymerization process. The pressure for liquid phase polymerization in a loop reactor is typically less than 1000 psig. Pressure for gas phase polymerization is usually at about 200 to about 500 psig. High pressure polymerization in tubular or autoclave reactors is generally run at about 20,000 to 75,000 psig. Polymerization reactors can also be operated in a supercritical region occurring at generally higher temperatures and pressures. Operation above the critical point of a pressure/temperature diagram (supercritical phase) may offer advantages.

The concentration of various reactants can be controlled to produce polymers with certain physical and mechanical properties. The proposed end-use product that will be formed by the polymer and the method of forming that product may be varied to determine the desired final product properties. Mechanical properties include, but are not limited to tensile strength, flexural modulus, impact resistance, creep, stress relaxation, crack growth, and hardness tests. Physical properties include, but are not limited to density, molecular weight, molecular weight distribution, melting temperature, glass transition temperature, temperature melt of crystallization, stereoregularity, short chain branching, long chain branching and rheological measurements.

The concentrations of monomer, co-monomer, hydrogen, co-catalyst, modifiers, and electron donors are generally important in producing specific polymer properties. Comonomer may be used to control product density. Hydrogen may be used to control product molecular weight. Co-catalysts may be used to alkylate, scavenge poisons and/or control molecular weight. The concentration of poisons may be minimized, as poisons may impact the reactions and/or otherwise affect polymer product properties. Modifiers may be used to control product properties and electron donors may affect stereoregularity.

In an embodiment, a method of preparing a polymer composition comprises contacting an olefin monomer (e.g., ethylene) with a catalyst system under conditions suitable for the formation of a polymer of the type described herein. In an embodiment, the catalyst system comprises a transition-metal complex. The terms "catalyst composition," "catalyst mixture," "catalyst system," and the like, do not depend upon the actual product resulting from the contact or reaction of the components of the mixtures, the nature of the active catalytic site, or the fate of the co-catalyst, the catalyst, any olefin monomer used to prepare a precontacted mixture, or the activator-support, after combining these components. Therefore, the terms "catalyst composition," "catalyst mixture," "catalyst system," and the like, can include both heterogeneous compositions and homogenous compositions.

In an embodiment, a catalyst system suitable for the preparation of a polymer composition comprises at least one metallocene-containing compound. Herein, the term "metallocene" describes a compound comprising at least one $\eta^3$ to $\eta^5$-cycloalkadienyl-type moiety, wherein $\eta^3$ to $\eta^5$-cycloalkadienyl moieties include cyclopentadienyl ligands, indenyl ligands, fluorenyl ligands, and the like, including partially saturated or substituted derivatives or analogs of any of these. Possible substituents on these ligands include hydrogen, therefore the description "substituted derivatives thereof" in this disclosure comprises partially saturated ligands such as tetrahydroindenyl, tetrahydrofluorenyl, octahydrofluorenyl, partially saturated indenyl, partially saturated fluorenyl, substituted partially saturated indenyl, substituted partially saturated fluorenyl, and the like.

In an embodiment, a catalyst system suitable for the preparation of a polymer composition comprises at least two metallocene-containing compounds. Nonlimiting examples of metallocene-containing compounds suitable for use in this disclosure are described in more detail in U.S. Pat. Nos. 4,939,217; 5,191,132; 5,210,352; 5,347,026; 5,399,636; 5,401,817; 5,420,320; 5,436,305; 5,451,649; 5,496,781; 5,498,581; 5,541,272; 5,554,795; 5,563,284; 5,565,592; 5,571,880; 5,594,078; 5,631,203; 5,631,335; 5,654,454; 5,668,230; 5,705,478; 5,705,579; 6,187,880; 6,509,427; 7,026,494, and U.S. Patent App. Nos. 20100190926 A1 and 20120059134, each of which is incorporated by reference herein in its entirety. Other processes to prepare metallocene compounds suitable for use in this disclosure have been reported in references such as: Koppl, A. Alt, H. G. J. Mol. Catal. A. 2001, 165, 23; Kajigaeshi, S.; Kadowaki, T.; Nishida, A.; Fujisaki, S. The Chemical Society of Japan, 1986, 59, 97; Alt, H. G.; Jung, M.; Kehr, G. J. Organomet. Chem. 1998, 562, 153-181; and Alt, H. G.; Jung, M. J. Organomet. Chem. 1998, 568, 87-112; each of which is incorporated by reference herein in its entirety. The following treatises also describe such methods: Wailes, P. C.; Coutts, R. S. P.; Weigold, H. in Organometallic Chemistry of Titanium, Zirconium, and Hafnium, Academic; New York, 1974; Cardin, D. J.; Lappert, M. F.; and Raston, C. L.; Chemistry of Organo-Zirconium and -Hafnium Compounds; Halstead Press; New York, 1986. In an embodiment, the polymer composition is prepared using a catalyst system comprising two metallocene-containing compounds and may be characterized as a dual metallocene polymer or a dual metallocene resin. In an embodiment such dual-metallocene catalysts may be used to prepare resins of the type disclosed herein.

In an embodiment, the dual metallocene catalyst used for preparation of the polymer composition comprises an unbridged metallocene, designated MTE-A. In an embodiment, MTE-A is a compound that may be characterized by one of general formulas 1 or 2:

Formula 1

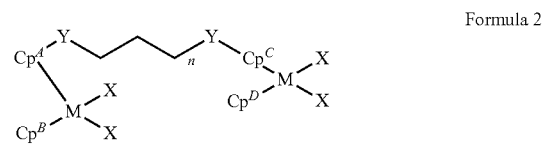

Formula 2 where each X is independently F, Cl, Br, I, methyl, benzyl, phenyl, H, $BH_4$, a hydrocarbyloxide group having up to 20 carbon atoms, a hydrocarbylamino group having up to 20 carbon atoms, a trihydrocarbylsilyl group having up to 20 carbon atoms, $OBR'_2$ wherein R' may be an alkyl group having up to 12 carbon atoms or an aryl group having up to 12 carbon atoms, and $SO_3R''$, wherein R" may be an alkyl group having up to 12 carbon atoms or an aryl group having up to 12 carbon atoms; Y is a $CR_2$ or $SiR_2$ group where R is hydrogen or a hydrocarbyl group; $Cp^A$, $Cp^B$, $Cp^C$, and $Cp^D$ are each independently a substituted or unsubstituted cyclopentadienyl group, indenyl group, or flourenyl group and where any substituent on $Cp^A$, $Cp^B$, $Cp^C$, and $Cp^D$ can be H, a hydrocarbyl group having up to 18 carbon atoms or a hydrocarbylsilyl group having up to 18 carbon atoms. In an embodiment, MTE-A is a dinuclear compound wherein each metal moiety has the same structural characteristic described previously herein.

In an embodiment, the dual metallocene catalyst used for preparation of the polymer composition further comprises a bridged metallocene compound hereinafter designated MTE-B. In an embodiment, MTE-B can be characterized by one of general formulas 3 or 4:

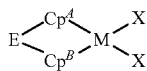

Formula 3

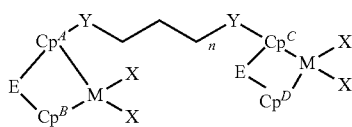

Formula 4 where M is Ti, Zr or Hf; each X is independently F, Cl, Br, I, methyl, phenyl, benzyl, H, $BH_4$, a hydrocarbyloxide group having up to 20 carbon atoms, a hydrocarbylamino group having up to 20 carbon atoms, a trihydrocarbylsilyl group having up to 20 carbon atoms, $OBR'_2$ wherein R' may be an alkyl group having up to 12 carbon atoms or an aryl group having up to 12 carbon atoms, or $SO_3R''$ wherein R" may be an alkyl group having up to 12 carbon atoms or an aryl group having up to 12 carbon atoms; Y is a $CR_2$, $SiR_2$, or $R_2CCR_2$ group which may be linear or cyclic and where R is hydrogen or a hydrocarbyl group; $Cp^A$, $Cp^B$, $Cp^C$, and $Cp^D$ are each independently a substituted or unsubstituted cyclopentadienyl group, indenyl group, or flourenyl group and where any substituent on $Cp^A$, $Cp^B$, $Cp^C$, and $Cp^D$ can be H, a hydrocarbyl group having up to 18 carbon atoms or a hydrocarbylsilyl group having up to 18 carbon atoms. E represents a bridging group which may comprise (i) a cyclic or heterocyclic moiety having up to 18 carbon atoms, (ii) a group represented by the general formula $E^A R^{3A} R^{4A}$, wherein $E^A$ is C, Si, Ge, or B, and $R^{3A}$ and $R^{4A}$ are independently H or a hydrocarbyl group having up to 18 carbon atoms, (iii) a group represented by the general formula $-CR^{3B}R^{4B}-CR^{3C}R^{4C}-$, wherein $R^{3B}$, $R^{4B}$, $R^{3C}$, and $R^{4C}$ are independently H, or a hydrocarbyl group having up to 10 carbon atoms, or (iv) a group represented by the general formula $SiR_2-CR_2$ where X is Si or C and R is a hydrogen or hydrocarbyl group; or $-SiR^{3D}R^{4D}-SiR^{3E}R^{4E}-$, wherein $R^{3D}$, $R^{4D}$, $R^{3E}$, and $R^{4E}$ are independently H or a hydrocarbyl group having up to 10 carbon atoms, and wherein at least one of $R^{3A}$, $R^{3B}$, $R^{4A}$, $R^{4B}$, $R^{3C}$, $R^{4C}$, $R^{3D}$, $R^{4D}$, $R^{3E}$, $R^{4E}$ or the substituent on Cp, $Cp_1$, or $Cp_2$, is (1) a terminal alkenyl group having up to 12 carbon atoms or (2) a dinuclear compound wherein each metal moiety has the same structural characteristic as MTE-B.

The polymer composition may comprise additives. Examples of additives include, but are not limited to, antistatic agents, colorants, stabilizers, nucleators, surface modifiers, pigments, slip agents, antiblocks, tackifiers, polymer processing aids, and combinations thereof. Such additives may be used singularly or in combination and may be contacted with the polymer before, during, or after preparation of the polymer composition as described herein. Such additives may be added via any suitable technique, for example during an extrusion or compounding step such as during pelletization or subsequent processing into an end use article.

In an embodiment, the polymer composition comprises polyethylene. For example the polymer composition may comprise a polyethylene homopolymer. It is to be understood that an inconsequential amount of comonomer may be present in the polymers disclosed herein and the polymer still be considered a homopolymer. Herein an inconsequential amount of a comonomer refers to an amount that does not substantively affect the properties of the polymer disclosed herein. For example a comonomer can be present in an amount of less than about 0.5 wt. %, 0.1 wt. %, or 0.01 wt. % based on the total weight of polymer.

In an alternative embodiment, the polymer composition comprises a polyethylene copolymer. Examples of suitable comonomers include without limitation unsaturated hydrocarbons having from 3 to 20 carbon atoms such as propylene, 1-butene, 1-pentene, 1-hexene, 3-methyl-1-butene, 4-methyl-1-pentene, 1-heptene, 1-octene, 1-nonene, 1-decene, and mixtures thereof. In some embodiments the polymer composition is copolymer of ethylene and 1-hexene. The applicability of the aspects and features disclosed herein to linear olefin polymers other than ethylene (e.g., propylene and 1-butylene) and olefin copolymers are also contemplated.

In an embodiment, a polymer composition of the type described herein (e.g., PE) comprises a polymer blend, e.g., a blend of two or more component polymers. For example, the polymer composition may be a physical or mechanical blend of polymers, alternatively the polymer composition may be a reactor blend of polymers. In an embodiment, a process for the preparation of a polymer composition of the type disclosed herein comprises the preparation of each component of the polymer composition independent of the other components. The process may comprise polymerization of an alpha-olefin monomer in the presence of a catalyst system under a first set of reaction conditions to form a first component of the polymer composition. The process may further comprise polymerization of an alpha-olefin in the presence of a catalyst system under a second set of reaction conditions to form a second component of the polymer composition. The formation of the second component may be carried out in the presence of the first component (e.g., a reactor blend) or in the absence of the first component (and the two components subsequently blended, for example via mechanical blending, co-extrusion, etc.). A process for preparation of a polymer composition may further comprise contacting the first and second components utilizing any appropriate methodology (e.g., mechanical mixing). In such an embodiment, the resultant polymer composition comprises a physical blend of the first and second component.

Alternatively, a process for the preparation of a polymer composition of the type disclosed herein comprises polymerization of an alpha-olefin monomer in the presence of at least two different catalytic materials or catalysts, for example a catalyst system comprising at least two transition metal complexes. For example, the catalyst system may comprise a first and a second transition metal complex wherein the first and second transition metal complexes are different. In an embodiment, the catalyst system comprises at least two metallocene complexes and results in the simultaneous formation of at least two components of the polymer composition when both catalysts are employed in a single reactor. In the alternative, a first catalyst system comprising a first metallocene complex is associated with a first reactor. Alpha-olefin monomer may be contacted with the first catalyst system in the first reactor and conditions adjusted such that polymerization of the alpha-olefin monomer and a first component of the polymer composition is produced. The first component may then be contacted with a second catalyst system and alpha-olefin monomer under conditions to result in the polymerization of the alpha-olefin monomer and formation of the second component of the polymer composition. In such an embodiment, the components of the polymer composition are produced sequentially. In the aforementioned embodiments employing at least two metallocene complexes, the polymer composition formed may be described as a reactor blend of the two components.

A polymer composition of the type described herein may be a multimodal resin. Herein, the "modality" of a polymer resin refers to the form of its molecular weight distribution curve, i.e., the appearance of the graph of the polymer weight fraction as a function of its molecular weight, as may be displayed by, for example, gel permeation chromatography (GPC). The polymer weight fraction refers to the weight fraction of molecules of a given size. A polymer having a molecular weight distribution curve showing a single peak may be referred to as a unimodal polymer, a polymer having a curve showing two distinct peaks may be referred to as bimodal or a bimodal-like polymer, a polymer having a curve showing three distinct peaks may be referred to as trimodal polymer, etc. Polymers having molecular weight distribution curves showing more than one peak may be collectively referred to as multimodal polymers or resins. It is acknowledged that, in some instances, a multimodal polymer may appear to have a single peak via, for example, GPC analysis, when in fact the polymer itself is multimodal. In such instances, overlap of peaks may obscure the presence of other peaks and may imply unimodality, when in fact multimodality is a more accurate representation of the nature of the polymer.

In an embodiment, the polymer composition is characterized as a bimodal resin. A GPC of a polymer composition of the type described herein may display the following identifiable features (i) a peak attributable to a higher molecular weight (HMW) component and (ii) a peak attributable to a lower molecular weight (LMW) component. It is to be understood that a LMW component corresponds to a subpopulation of the polymer composition which on a GPC profile will show a distribution of molecular weights (e.g., Schulz-Flory, Gaussian) centered around some peak maximum value or range that has a lesser numerical value than the HMW component which is another subpopulation of the polymer composition also characterized by a distribution with a peak maximum value or range. In an embodiment, a GPC plot of the polymer composition exhibits a LMW component that is baseline separated from the HMW component. In an alternative embodiment, a GPC plot of the polymer composition exhibits a LMW component that is not baseline separated from the HMW component. In such embodiments, the GPC plot may be deconvoluted using any suitable methodology to extract the independent GPC profiles of the LMW and HMW components.

In an embodiment, the HMW component is present in a weight percentage based on the total weight of the polymer composition of from about 20% to about 80%, alternatively from about 30% to about 70%, or alternatively from about 40% to about 60% with the remainder of the composition primarily being the LMW component.

The LMW component may be characterized by a $M_w$ of less than about 50 kg/mol, alternatively less than about 45 kg/mol, or alternatively less than about 40 kg/mol. In an embodiment, the $M_w$ of the LMW component ranges from about 10 kg/mol to about 50 kg/mol. The HMW component may be characterized by a $M_w$ of greater than about 50 kg/mol, alternatively greater than about 65 kg/mol, alternatively greater than about 100 kg/mol, or alternatively from about 51 kg/mol to about 100 kg/mol. The $M_w$ describes the molecular weight distribution of the polymer composition and is calculated according to equation 1:

$$M_w = \frac{\sum_i N_i M_i^2}{\sum_i N_i M_i} \quad (1)$$

where $N_i$ is the number of molecules of molecular weight $M_i$. As used herein $M_w$ is measured by gel permeation chromatography.

In an embodiment, the LMW component may have a peak molecular weight ($M_p$) ranging from about 20 kg/mol to about 50 kg/mol, alternatively from about 25 kg/mol to about 50 kg/mol, or alternatively from about 30 kg/mol to about 45 kg/mol. In an embodiment, the HMW component may have an $M_p$ ranging from about 50 kg/mol to about 80 kg/mol, alternatively from about 60 kg/mol to about 80 kg/mol, or alternatively from about 65 kg/mol to about 75 kg/mol. The peak molecular weight is herein refers to the molecular weight of the highest peak as measured by gel permeation chromatography and is defined as the peak of the discernable maxima of $d_w/d_{log\ M}$.

As will be understood by one of ordinary skill in the art, the location of $M_w$ for a particular composition will be dependent on a variety of factors such as the polydispersity index of the composition, the value and type of the molecular weight distribution, the weight average molecular weight, and the like.

In one or more embodiments, polymer compositions of the type described herein are characterized by a density of from about 0.92 g/cc to about 0.96 g/cc, or from about 0.93 g/cc to about 0.95 g/cc, or from about 0.94 g/cc to about 0.95 g/cc as determined in accordance with ASTM D1505.

The polymer composition may further be characterized by a peak height ratio of the higher molecular weight component to the lower molecular weight component (HMW/LMW) of from about 0.8 to about 2.0, alternatively equal to or greater than about 1.0, alternatively equal to or greater than about 1.25, or alternatively equal to or greater than about 1.50. As used herein, peak height is defined as $d_w/d_{log\ M}$ at the $M_p$.

The polymer composition may further be characterized by a particle size distribution ratio (D90/D10) of from about 2 to about 5, alternatively greater than about 2, alternatively greater than about 2.5, or alternatively greater than about 3. D10 and D90 refer to the cumulative undersize distribution which notes the percentage of particles (i.e., 10% or 90%) having sizes at or below the indicated value. The D10 and D90 values may be determined by standard particle size measurements such as physically sifting the material, measuring the mass of each fraction and calculating that fraction as a percentage of the total.

In an embodiment, a method of the present disclosure comprises determining the heterogeneity of a polymer composition of the type disclosed herein, for example a multimodal (e.g., bimodal) polyethylene polymer composition. The polymer composition whose heterogeneity is being evaluated may be in the form of fluff where fluff refers to the product formed at the end of the polymerization process and obtained from the polymerization reactor. The method for determining the heterogeneity of the polymer composition as a whole (e.g., fluff) may comprise sieving the fluff into subpopulations on the basis of particle size. As used herein, particle size may be determined in accordance with the ability of a polymer particle to pass through a woven wire test sieve as described in ASTM E11-09. For purposes of this disclosure, all references to a woven wire test sieve refer to a woven wire test sieve as described in ASTM E11-09. As used herein, reference to particle size refers to the size of an aperture (e.g., nominal aperture dimension) through which the polymer particle will pass, and for brevity this is referred to herein as "particle size." An aperture is an opening in a sieve (e.g., woven wire test sieve) or a screen for particles to pass through. The aperture of the woven wire test sieve is a square and the nominal aperture dimension refers to the width of the square aperture. For example, a polymer particle is considered to have a size of less than about 2.00 mm if the polymer particle passes through the aperture of a 10 mesh woven wire test sieve, where the mesh size is given based on U.S. Sieve Series. As will be appreciated by one of skill in the art, and with the help of this disclosure polymer particles can have a plurality of shapes, such as for example cylindrical, discoidal, spherical, tabular, ellipsoidal, equant, irregular, or combinations thereof. Generally, for a particle to pass through an aperture of a sieve or screen, it is not necessary for all dimensions of the particle to be smaller than the aperture of such screen or sieve, and it could be enough for one of the dimensions of the particle to be smaller than the aperture of such screen or sieve. For example, if a cylindrical shaped particle that has a diameter of 1.00 mm and a length of 2.50 mm passes through the aperture of a 10 mesh woven wire test sieve, where the mesh size is according to U.S. Sieve Series, such particle is considered to have a particle size of less than about 2.00 mm.

In an embodiment, a polymer composition of the type disclosed herein in fluff form is sieved into a plurality of subpopulations based on particle size. The polymer composition as a whole (e.g., fluff) may be subjected to at least 3 sieves to produce at least 3 subpopulations, alternatively at least 4 sieves to produce at least 4 subpopulations, or alternatively at least 5 sieves to produce at least 5 subpopulations. In an embodiment, the sieves may have any suitable mesh size, for example the sieves may range in mesh size from about 10 to about 300, or alternatively from about 20 to about 200 based on the U.S. Sieve Series. Herein each subpopulation is denoted δx where x represents the mesh size of the subpopulation. For example, a polymer composition of the type disclosed herein (e.g., fluff) may be sieved into subpopulations such as $\delta_{10}$, $\delta_{25}$, $\delta_{50}$, and $\delta_{100}$. Typically, if every particle has the same molecular weight profile, despite its size, an overlay of the profiles on the same plot would show nearly indistinguishable curves. In an embodiment, the method comprises calculating the standard deviation in the dw/dlog M response for each data set (e.g., $\delta_{25}$) at selected log M values and then summing the results to produce a heterogenity value designated by the symbol Ψ.

In an embodiment, the standard deviation of the MW for the polymer composition as a whole is calculated using Formula 1

$$\sigma = \sqrt{\frac{\sum(x-\bar{x})^2}{N}}$$

where σ is the standard deviation, χ is the MW for each subpopulation $\bar{x}$ is the mean of the values and N is the number of values. Without wishing to be limited by theory, a low value for Ψ indicates that despite variations in particle size the polymer molecules have similar structure and result in MWs that overlap substantially, in other words the polymer composition as a whole (i.e., fluff) comprises particles that vary in particle size but have similar microstructure. In an embodiment, the polymer composition is a metallocene-catalyzed bimodal polyethylene with a low Ψ value ranging from about 0.35 to about 3.0, alternatively from greater than zero to less than about 3.0, alternatively from greater than zero to less than about 2.0, alternatively from greater than zero to less than about 1.5, alternatively from greater than zero to less than about 1.0, or alternatively from greater than zero to less than about 0.5, or alternatively about zero. Such polymer compositions having a low Ψ value within the disclosed ranges form polymer articles having a low gel count. In contrast, higher values of Ψ indicate that in addition to variations in particle size, the polymer molecules within the polymer composition as a whole (i.e., fluff) differ in microstructure to an extent that results in a decreased level of heterogeneity and result in articles having a higher gel count. Herein a high gel count refers to greater than about 100 gels/ft$^2$ while a low gel refers to less than about 100 gels/ft$^2$.

In an embodiment, a method further comprises predicting a gel count for a polymer composition, for example a multimodal (e.g., bimodal) polyethylene polymer composition, based upon the heterogeneity thereof. In one or more embodiments, the gel count is predicted based on the heterogeneity of the sample in accordance with Equation 2:

$$\text{Log }10(\text{Gels})=1.34171+0.576990P)+7.15E-03(\text{HMW }M_p)-0.12448(\text{LMW }M_r)-1.74228(\text{HMW }M_p/\text{LMW }M_p) \quad \text{(Equation 2)}$$

wherein Gels is gel count, Ψ is the heterogeneity value, HMW $M_p$ is a higher molecular weight component peak, LMW $M_p$ is a lower molecular weight component peak and HMW/LMW is the peak height ratio of the HMW component and the LMW component. The peak molecular weight refers to the molecular weight at which the highest absorption on the y-axis is obtained.

In an embodiment, the method further comprises predicting the gel count for a polymer composition utilizing Equation 2 and fabricating an article (e.g., film) from a polymer composition predicted to have a low gel count (e.g., less than about 100 gels/ft$^2$). As will be understood the by one of ordinary skill in the art, utilization of equation 2 to predict the gel count of a polymer composition as a whole will involve determining the Ψ value as described previously herein.

In an embodiment, the method may further comprise determining the actual gel count in the article fabricated from a polymer composition of the type disclosed herein. In such embodiments, a comparison of the predicted and actual gel count may be carried out using any suitable mathematical metric or analytical methodology for comparison of the actual and predicted gel counts. As utilized herein, the actual gel count of the article may be determined using any suitable methodology, for example by optical measurement or by visual assessment (e.g., counting the number of gels per unit area).

In an embodiment, a polymer composition of the type disclosed herein is predicted to generate articles having high gel counts (i.e., greater than 100 gels/ft$^2$). In such embodiments, (i) the polymer composition may be deemed unsuitable for use in its intended application (e.g., film formation) and discarded or utilized in a different application; (ii) one or more parameters of the polymerization reaction utilized in the production of the polymer composition may be adjusted to facilitate the production of polymer compositions having low predicted gel counts; and/or (iii) the polymer composition may be separated into one or more subpopulations (e.g., sieved as described herein or otherwise physically separated by particle size) and at least two of the subpopulations combined to produce a second polymer composition having a lower degree of heterogeneity than the first/parent polymer composition.

In an embodiment, a polymer composition of the type disclosed herein is predicted to generate articles having gel counts that are greater than some user and/or process desired range or value (e.g., greater than 100 gels/ft$^2$). In such embodiments, the polymerization reaction utilized in production of the polymer composition may be adjusted to facilitate the production of a polymer composition that would have a gel count that is within some user and/or process desired range. Such adjustments may be made using any suitable methodology to modify the polymer architecture. In some embodiments, adjustments to the polymerization reaction conditions are made on the fly (e.g., in real time). For example, the polymer composition may be a sample taken under a particular set of polymerization reaction conditions. Prior to the production of an intended quantity of polymer (e.g., a commercial batch or run), the gel count of a sample of the polymer composition being produced may be predicted and the polymerization reaction conditions adjusted in real time (e.g., during the polymerization run) to affect the gel count of the remaining amount of polymer to be produced.

In an embodiment, a polymer composition of the type disclosed herein is predicted to generate articles having gel counts that are greater than some user and/or process desired range or value. In such embodiments, the polymer composition may be sieved to produce a plurality of subpopulations characterized by the polymer particle size (e.g., $\delta_{25}$). In an embodiment, at least two of the subpopulations having similar MW values are combined to produce a low heterogeneity polymer composition (LHPC) that is subsequently utilized to fabricate an article. Herein similar MW values refer to values that differ by from about 1% to about 20%, alternatively from about 5% to about 20%, or alternatively less than about 15%. The gel count of the LHPC may be further predicted via the heterogeneity value thereof as described herein, and the predicted gel count can be compared to an actual gel count as described herein.

It is contemplated that the heterogeneity of the polymer composition is related to a number of processability characteristics displayed by the composition. In an embodiment, the heterogeneity of the polymer composition is utilized to predict the high load melt index (HLMI) of the polymer composition. For example, the heterogeneity of a polymer composition of the type disclosed herein may exhibit a high load melt index (HLMI) that corresponds to the following relationship set forth in Equation 3:

$$1/[(\text{HLMI})^2] = -0.53341 - 9.33\text{E}{-03}(\Psi) + 2.04\text{E}{-04}(\text{HMW M}_p) + 0.010454(\text{LMW M}_p) + 0.57288(\text{HMW M}_p/\text{LMW M}_p) \quad (\text{Equation 3})$$

wherein $\Psi$ is the heterogeneity value, HMW $M_p$ is the peak molecular weight of the HMW component, LMW $M_p$ is the peak molecular weight of the LMW component, and HMW $M_p$/LMW $M_p$ is the peak height ratio for the $M_p$ of the HMW and LMW component. In an embodiment, a method of the present disclosure comprises obtaining the heterogeneity value, HMW, LMW $M_p$, and HMW $M_p$/LMW for a polymer sample and predicting the HLMI of the polymer sample using Equation 3. The method may further comprise determining the HLMI of the polymer sample utilizing any suitable methodology, for example in accordance with ASTM D1238. In some embodiments, the method may further comprise comparing the predicted HLMI of the polymer sample to the actual HLMI of the polymer sample.

The high load melt index (HLMI) refers to the rate a polymer which can be forced through an extrusion rheometer orifice of 0.0824 inch diameter when subjected to a force of 21,600 grams at 190° C. in accordance with ASTM D 1238. In one or more embodiments, the polymer composition exhibits a HLMI of from about 0.1 g/10 min to about 100 g/10 min, or from about 1 g/10 min to about 75 g/10 min, or from about 1 g/10 min to about 50 g/10 min, or at least about 6 g/10 min, as determined in accordance with ASTM D1238-F.

In one or more embodiments the polymer composition produced as disclosed herein may be formed into an article. For example, a polymer composition may be extruded into a sheet, which is then thermoformed into an end use article such as a container, a cup, a tray, a pallet, a toy, or a component of another product. In an embodiment, a polymer composition produced as described herein (e.g., polyethylene) may be formed into films which can be useful in food packaging.

In one or more embodiments the polymer composition produced as disclosed herein may be formed into films. The films of this disclosure may be produced by any suitable method and under any suitable conditions for the production of films. In an embodiment, the polymer composition is formed into films through a cast film process. In a cast film process, plastic melt is extruded through a slit die onto a chilled, polished roll to freeze the film. The speed of the roll controls the draw down ratio and film gauge. The film moves forward toward a second wounding roll where cooling is completed.

In another embodiment, the polymer compositions disclosed herein are formed into films through a blown film process. Blown film processes may include forcing molten polymer through a circular die, which is then blown. The resultant bubble is then flattened and cut into strips, that when rolled, produces rolls of flat film.

The films formed from the polymer compositions disclosed herein may be of any thickness desired by the user. Alternatively, the polymer compositions of this disclosure may be formed into films having a thickness of from about 0.3 mils (7 microns) to about 3 mils (76 microns), or from about 0.5 mils (12 microns) to about 2 mils (50 microns), or from about 0.8 mil (20 microns) to about 1.6 mils (40 microns).

In an embodiment, films formed from a polymer composition of the type disclosed herein are characterized by gels counts of from about 10 gels/ft$^2$ to about 100 gels/ft$^2$, alternatively from about 10 gels/ft$^2$ to about 75 gels/ft$^{2'}$ or alternatively from about 10 gels/ft$^2$ to about 50 gels/ft$^2$.

In an embodiment, a method of the present disclosure comprises obtaining at least one polymer sample having a LMW component and a HMW component. The polymer sample may be obtained in an amount corresponding to a laboratory scale production, e.g., 1 kilogram or less quantities or an amount corresponding to a commercial scale production; e.g., 1000 kg or more. Thus amounts of polymer corresponding to a laboratory scale production process are designated laboratory scale amount. Herein amounts of polymer corresponding to a commercial scale production process are designated bulk polymer.

In an embodiment, the methodologies disclosed herein may facilitate the production of polymer compositions tailored to some user and/or process desired gel count level. For example, at least one laboratory scale amount of a polymer sample may be obtained and separated into a plurality of polymer sample subpopulations using any suitable methodology. For example, the plurality of polymer sample subpopulations may be obtained by sieving of the laboratory scale amount of polymer sample into subpopulations on the basis of particle size. In such embodiments, the polymer sample subpopulations may be utilized to determine the heterogeneity value for the laboratory scale amount of polymer sample using the methodologies disclosed herein (e.g., standard deviation of the MWD). Further, the weight fraction each subpopulation contributes to the polymer sample as a whole may be determined. The resulting information would provide a subpopulation (e.g., $\delta_{100}$, corresponding to a 100 mesh particle size subpopulation), a weight fraction of that subpopulation (e.g., 0.3/1) and a heterogeneity value (e.g., 1.2). In an embodiment, a bulk polymer sample is obtained. The bulk polymer sample may be separated into subpopulations samples corresponding to the subpopulations produced by separation of the laboratory scale polymer samples. In an embodiment, at least one of the subpopulations generated by the bulk polymer sample is characterized by a heterogeneity value of less than about 3 and subsequently utilized to produce a polymer article. Alternatively at least two of the subpopulations generated by the bulk polymer sample are combined to generate a formulated resin. The formulated resin may be made by the combining of any number of subpopulations of the bulk polymer sample that results in a heterogeneity value of less than 3. Further, the formulated resin may be made by the combining of subpopulations of the bulk polymer sample that generates a heterogeneity value of less than about 3 while maximizing the weight fraction of bulk polymer sample used. For example, the subpopulations may be combined to generate a heterogeneity value of less than about 3 and utilize a weight fraction of polymer sample ranging from about 0.2 to about 0.9, alternatively from about 0.3 to about 0.8, or alternatively from about 0.4 to about 0.6 of the bulk polymer sample. In some embodiments, the bulk polymer sample has a heterogeneity value of greater than about 3 and the use of subpopulations to generate a formulated resin having a heterogeneity value of less than about 3 rehabilitates a bulk polymer sample having poor processing characteristics (e.g., a predicted high gel count) and results in the recovery of the maximum amount of the bulk polymer sample having some desired processing characteristics. In an alternative embodiment, the bulk polymer sample has a heterogeneity value of less than about 3 and subpopulations of the bulk polymer sample may be utilized to generate a formulated resin having a heterogeneity value within a user-desired range or for a particular set of applications. For example, a bulk polymer sample having a low heterogeneity value may be used to generate subpopulations with even lower heterogeneity values predicted to generate an article with ultra-low gels (e.g., less than about 20 gels/ft$^2$). As apparent from the present disclosure, the methodologies described herein may be utilized to generate resins having processing characteristics tailored to some desired specification (e.g., particular gel count level).

FIG. 1 illustrates a computer system 980 suitable for implementing one or more embodiments disclosed herein. For example, the results of determining one or more metrics for a fluff (i.e. polymer composition as a whole) and/or one or more subpopulations of the composition (e.g., sieved sample) may be transmitted to a computer system which can then determine one or more parameters (e.g., compositional diversity) and/or predicted gel count. The computer system 980 includes a processor 982 (which may be referred to as a central processor unit or CPU) that is in communication with memory devices including secondary storage 984, read only memory (ROM) 986, random access memory (RAM) 988, input/output (I/O) devices 990, and network connectivity devices 992. The processor 982 may be implemented as one or more CPU chips.

It is understood that by programming and/or loading executable instructions onto the computer system 980, at least one of the CPU 982, the RAM 988, and the ROM 986 are changed, transforming the computer system 980 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by any suitable design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 984 is typically comprised of one or more disk drives or tape drives and is used for non-volatile storage of data and as an over-flow data storage device if RAM 988 is not large enough to hold all working data. Secondary storage 984 may be used to store programs which are loaded into RAM 988 when such programs are selected for execution. The ROM 986 is used to store instructions and perhaps data which are read during program execution. ROM 986 is a non-volatile memory device which typically has a small memory capacity relative to the larger memory capacity of secondary storage 984. The RAM 988 is used to store volatile data and perhaps to store instructions. Access to both ROM 986 and RAM 988 is typically faster than to secondary storage 984. The secondary storage 984, the RAM 988, and/or the ROM 986 may be referred to in some contexts as computer readable storage media and/or non-transitory computer readable media.

In an embodiment, GPC chromatographs for the polymer composition as a whole, or subpopulations of the samples may be transmitted to the computer system 980. Software designed to extract information relevant to the prediction of processability parameters such as Mp and $\Psi$ may be utilized to ascertain the values for the variables present in Equations 2 or 3. Further such software may be designed to output values for predicted gel count and HLMI based solely on the input of GPC chromatographs.

I/O devices 990 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 992 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. These network connectivity devices 992 may enable the processor 982 to communicate with the Internet or one or more intranets. With such a network connection, it is contemplated that the processor 982 might receive information from the network, or might output information to the network in the course of performing the above-described method steps. Such information, which is often represented as a sequence of instructions to be executed using processor 982, may be received from and outputted to the network, for example, in the form of a computer data signal embodied in a carrier wave.

Such information, which may include data or instructions to be executed using processor 982 for example, may be received from and outputted to the network, for example, in the form of a computer data baseband signal or signal embodied in a carrier wave. The baseband signal or signal embodied in the carrier wave, or other types of signals currently used or hereafter developed, may be generated according to several methods well known to one skilled in the art. The baseband signal and/or signal embodied in the carrier wave may be referred to in some contexts as a transitory signal.

The processor 982 executes instructions, codes, computer programs, scripts which it accesses from hard disk, floppy disk, optical disk (these various disk based systems may all be considered secondary storage 984), ROM 986, RAM 988, or the network connectivity devices 992. While only one processor 982 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 984, for example, hard drives, floppy disks, optical disks, and/or other device, the ROM 986, and/or the RAM 988 may be referred to in some contexts as non-transitory instructions and/or non-transitory information.

In an embodiment, the computer system 980 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 980 to provide the functionality of a number of servers that is not directly bound to the number of computers in the computer system 980. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 980, at least portions of the contents of the computer program product to the secondary storage 984, to the ROM 986, to the RAM 988, and/or to other non-volatile memory and volatile memory of the computer system 980. The processor 982 may process the executable instructions and/or data structures in part by directly accessing the computer program product, for example by reading from a CD-ROM disk inserted into a disk drive peripheral of the computer system 980. Alternatively, the processor 982 may process the executable instructions and/or data structures by remotely accessing the computer program product, for example by downloading the executable instructions and/or data structures from a remote server through the network connectivity devices 992. The computer program product may comprise instructions that promote the loading and/or copying of data, data structures, files, and/or executable instructions to the secondary storage 984, to the ROM 986, to the RAM 988, and/or to other non-volatile memory and volatile memory of the computer system 980.

In some contexts, the secondary storage 984, the ROM 986, and the RAM 988 may be referred to as a non-transitory computer readable medium or a computer readable storage media. A dynamic RAM embodiment of the RAM 988, likewise, may be referred to as a non-transitory computer readable medium in that while the dynamic RAM receives electrical power and is operated in accordance with its design, for example during a period of time during which the computer 980 is turned on and operational, the dynamic RAM stores information that is written to it. Similarly, the processor 982 may comprise an internal RAM, an internal ROM, a cache memory, and/or other internal non-transitory storage blocks, sections, or components that may be referred to in some contexts as non-transitory computer readable media or computer readable storage media.

In an embodiment, one or more metrics of the type disclosed herein for evaluating the compositional diversity of a fluff (i.e., polymer composition as a whole) are transmitted to a computer system of the type disclosed herein. The computer system may be characterized by software that utilizes the transmitted values to provide information to the user as to the propensity of the fluff (i.e., polymer composition as a whole) to form gels when fabricated into an article (e.g., film).

EXAMPLES

For each of the following examples molecular weights and molecular weight distributions were obtained using a PL 220 GPC/SEC high temperature chromatography unit (Polymer Laboratories, now an Agilent Company) with 1,2,4-trichlorobenzene (TCB) as the solvent, with a flow rate of 1 mL/minute at a temperature of 145° C. BHT (2,6-di-tert-butyl-4-methylphenol) at a concentration of 0.5 g/L was used as a stabilizer in the TCB. An injection volume of 400 µL was used with a nominal polymer concentration of 1.0 mg/mL. Dissolution of the sample in stabilized TCB was carried out by heating at 150° C. for about 5 hours with occasional, gentle agitation. The columns used were three PLgel 20 m Mixed A LS columns (7.5×300 mm) and were calibrated with the integral method using a broad linear polyethylene standard (Chevron Phillips Chemical Company Marlex® BHB 5003 polyethylene) for which the molecular weight distribution had been determined. An IR4 detector (Polymer Char, Spain) was used for the concentration detection.

Samples were extruded on a Davis Standard blown film line equipped with a barrier screw with a matrix mixing element under the following conditions to produce 1 mil films: 2 inch die, 0.035 inch die gap, 29 lbs/hr, 4.0:1 blow up ration, 14 inch frost-line height, 20/20 screen pack, 205 C extruder set temperature and 220 C die set temperature.

Gels greater than 200 microns were measured by the OCS FS5 equipment using 3 levels of gel detection (55, 48 and 10) and grey level set at 170.

Example 1

Figure 2:
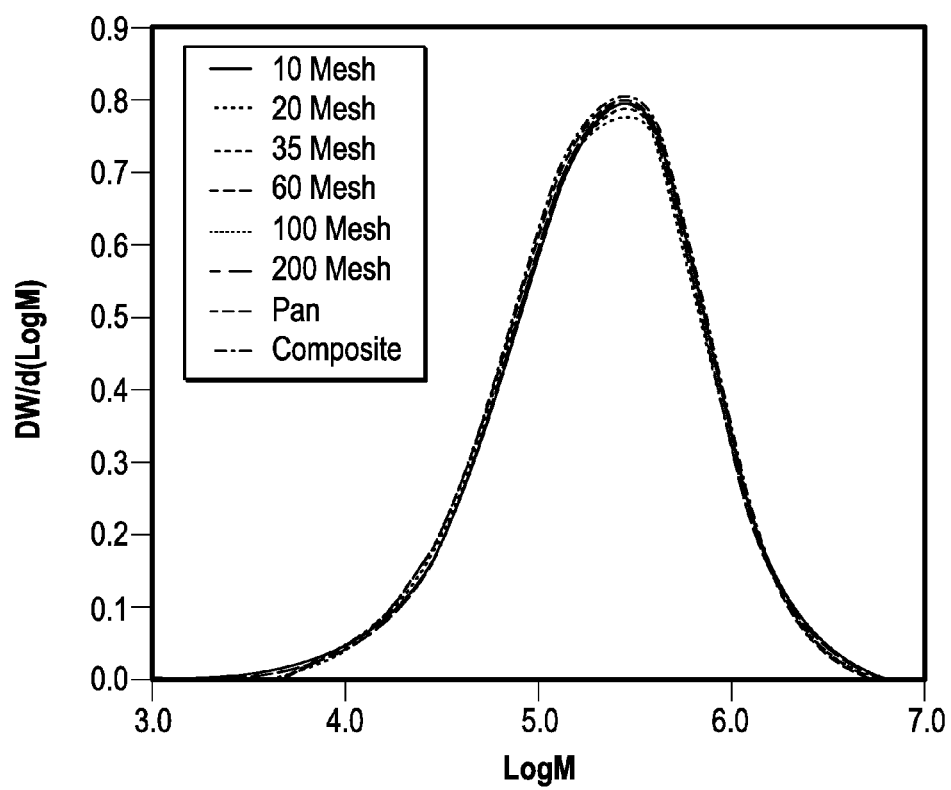
FIG. 2 depicts gel permeation chromatographs of sieved Ziegler-Natta catalyzed polymer samples.

Various processing parameters for dual metallocene bimodal polyethylene polymer samples were predicted on the basis of analysis of compositional heterogeneity of the type disclosed herein. Such heterogeneity was estimated by first measuring the molecular weight profiles of sieved fluff particles. In the following example, the compositional heterogeneity of the dual-metallocene bimodal polyethylene polymer samples is compared to that of a Ziegler Natta catalyzed polyethylene resin. FIG. 2 illustrates an overlay of molecular weight profiles of the Ziegler-Natta catalyzed polyethylene resin, and all GPC data was first interpolated so that there were 100 points between log 2.3 and log 8 wherein every particle has nearly the same profile, despite its size. Referring to FIG. 2, the Ziegler Natta catalyzed polyethylene polymer shows that the overlay of the profiles on the same plot produces nearly indistinguishable curves. Calculating the standard deviation in the dw/dlog M response for such a data set at selected log M values and then summing the results resulted in a very low heterogeneity value ($\Psi$=0.35 in this case), as expected.

Figure 3A:
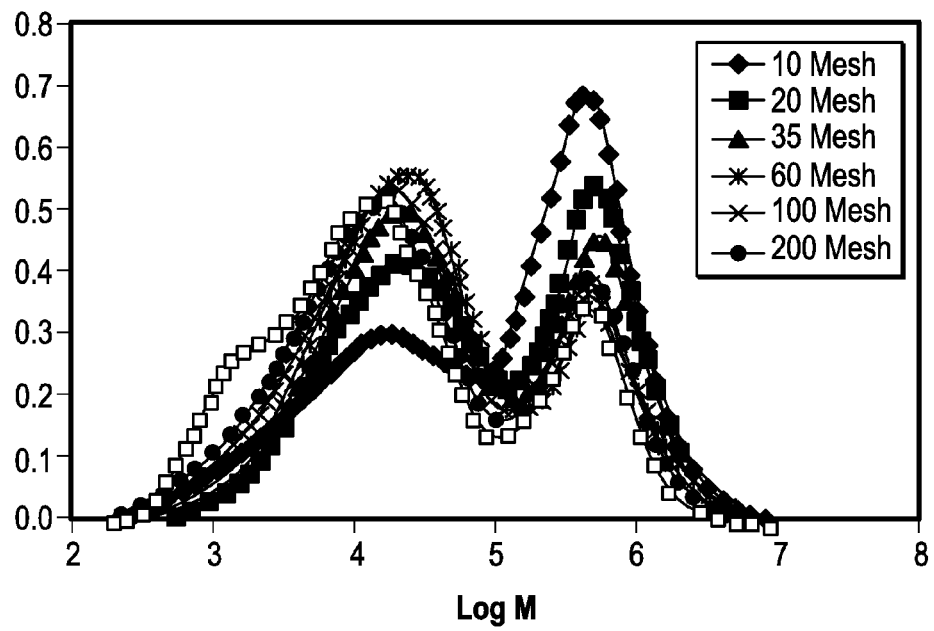
FIG. 3a is an overlay of gel permeation chromatographs for sieved polymer samples from example 1.
Figure 3B:
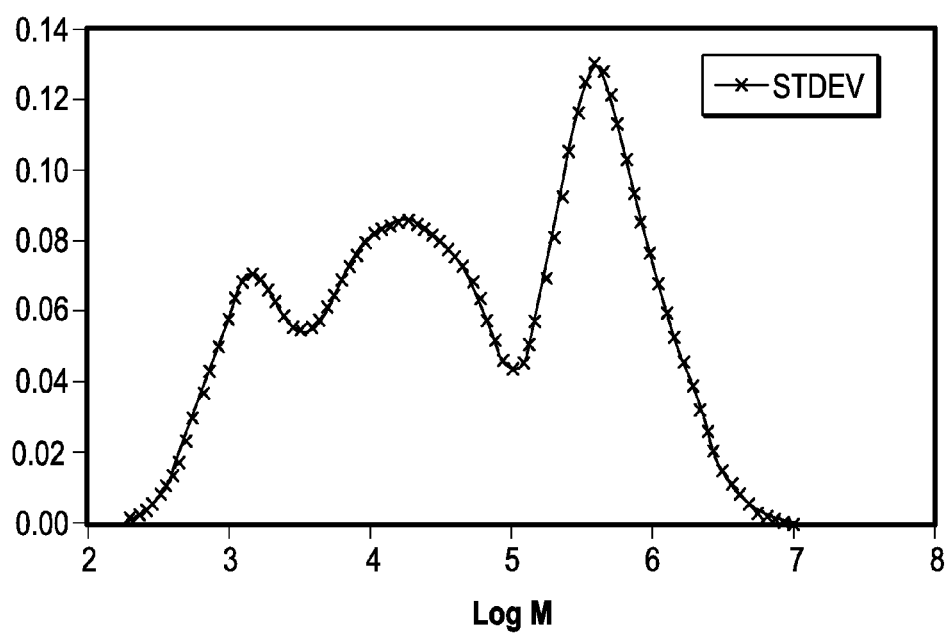
FIG. 3b is a plot of the heterogeneity values as a function of Log M for sieved polymer samples from a bimodal resin.

However, FIG. 3A shows a similar set of sieved fluff data from bimodal resins. The difference in the molecular weight distributions were characterized by a $\Psi$ value of 3.85 (over 10 times greater than the calculated value for the data set shown in FIG. 1). Furthermore, the difference between these molecular weight distributions obtained for the sieved data can also be represented as a plot of $\Psi$ values vs. Log M as shown in FIG. 3B.

It was noted that certain bimodal resins that have high $\Psi$ values for a set of sieved samples as demonstrated in FIG. 3A. In the top plot (FIG. 3A) the GPC data shows changes in MWD with particle size for sample 4A (1156 gel/ft$^2$). In plot 3B, (lower plot of the figure) heterogeneity is illustrated by plotting out values at a particular Log M values), also have high gel content when pelletized and subsequently blow into film.

Table 1 below compares several sets of dual metallocene bimodal polyethylene samples (designated samples 1A-5B) that have very similar GPC profiles of the pelletized sample, yet vastly different gel content. In these samples the molecular weight profiles were described in terms of the peak molecular weight ($M_r$) of the lower and higher molecular weight components as well as the peak height ratio of the two components (i.e., HMW $M_p$/LMW $M_p$). It was demonstrated in these examples that samples with high $\Psi$ values also had high gel content. For the samples in Table 1 gels are defined as gels>200 micron in size.

TABLE 1

| Resin | STDEV | LMW (kg/mol) | HMW (kg/mol) | HMW/LMW PKHT Ratio | Gels > 200 µ/ft$^2$ | Gel Class | |
|---|---|---|---|---|---|---|---|
| 1A | 3.0 | 21 | 568 | 0.9 | 3585 | 1 | Class 1 equals > 1000 |
| 1B | 2.2 | 21 | 568 | 0.9 | 9 | 2 | Class 2 equals < 100 |
| 2A | 2.7 | 21 | 568 | 1.0 | 1085 | 1 | |
| 2B | 1.4 | 21 | 568 | 1.0 | 31 | 2 | |
| 3A | 2.8 | 21 | 568 | 1.0 | 2000 | 1 | |
| 3B | 2.0 | 21 | 568 | 1.0 | 82 | 2 | |
| 4A | 2.7 | 21 | 568 | 1.1 | 1156 | 1 | |
| 4B | 2.3 | 21 | 568 | 1.1 | 53 | 2 | |
| 5A | 2.6 | 18 | 498 | 1.1 | 1112 | 1 | |
| 5B | 2.0 | 18 | 498 | 1.0 | 40 | 2 | |

The results summarized in Table 1 demonstrate that compositional heterogeneity as characterized by the standard deviation of the MWD of the sieved polymer samples can be useful as a single metric in identification of the propensity of a polymer sample to generate gels during processing. In this example each polymer sample was sieved into two subpopulations designated A and B. Thus polymer sample 1 was sieved into 2 samples, Sample 1A and Sample 1B. Samples 1A and 1B were chosen to have identical Mw for the LMW and HMW component and the same peak height ratio of the LMW/HMW component. The samples differed only in the standard deviation of the MWD. The results demonstrate that based solely on analysis of the standard deviation of the MWD, the polymer samples could be categorized into at least 2 classes, those having greater than 1000 gels/ft², Class 1, and those having less than 100 gels/ft², Class 2.

Figure 4:
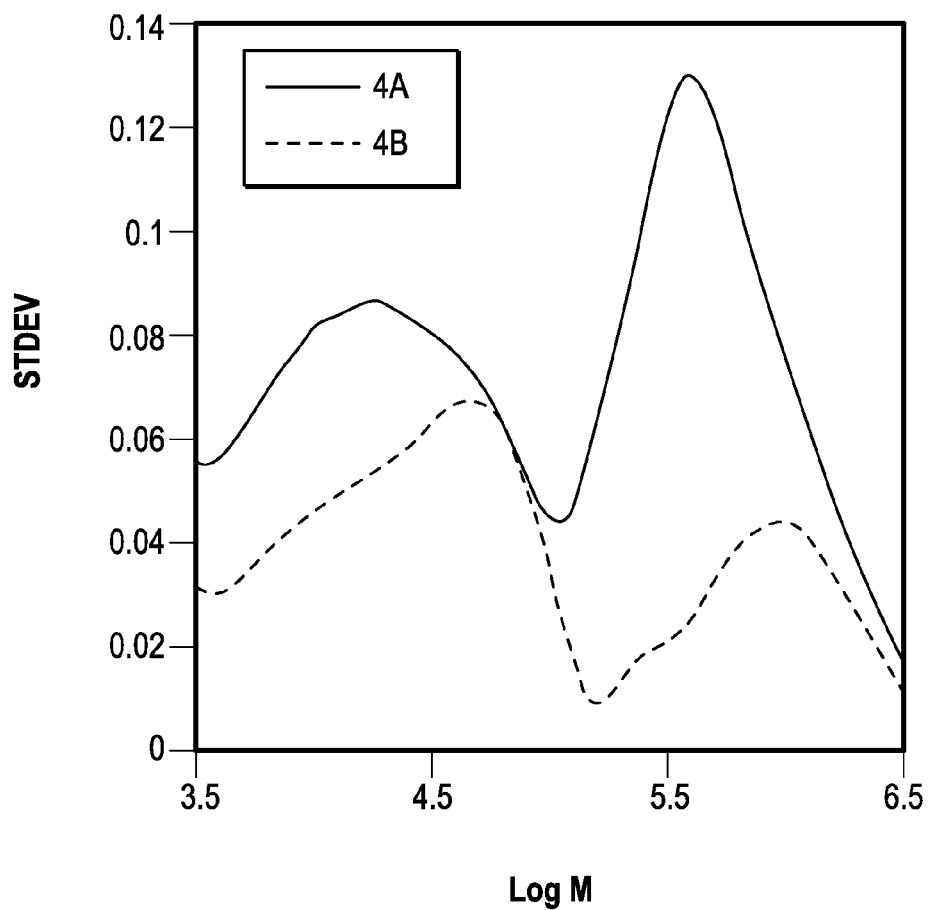
FIG. 4 is a comparative plot of heterogeneity values as a function of Log M for high gel samples (4A) and low gel samples (4B).

Moreover, when the Ψ vs. Log M plots were compared, a difference was observed in the Class 1 and Class 2 plots in that the Class 1 plots had larger Ψ values at the higher molecular weights (FIG. 4; comparative plots of Ψ vs Log M for high Ψ and sample 4A compared to low Ψ and sample 4B—only data between 3.5 and 6.5 Log M were used), e.g., the high Ψ value/Class 1 resin had more area under the plot curve and an amount of material at higher molecular weights than did the low Ψ/Class 2 samples.

Figure 5:
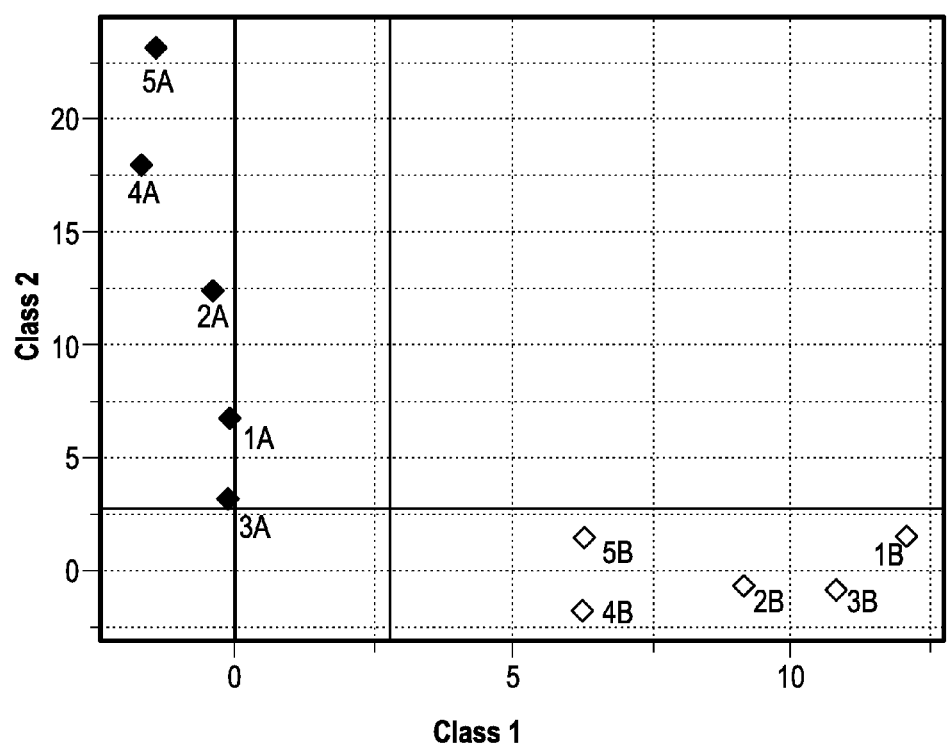
FIG. 5 is a Coomans plot of the heterogeneity values as a function of Log M for the samples from Example 1.

A comparison of the heterogeneity values as a function of Log M was made by performing a K nearest neighbors (KNN) analysis the results of which are depicted as FIG. 5, a Coomans plot. The Coomans plot as given in FIG. 5 shows the distance of any point from the center of a cluster. So, for example in FIG. 5, the x axis shows the distance from class C1, those points closest to the C1 cluster (low values of Class 1) are class C1, those points which are the farthest away are class C2, and those in the middle distances cannot be classed (convoluted). The y axis is just the converse, those points measure with reference to the center of C2 cluster. So in the plotted data the red diamonds are >5 distance from the clustering of the Class 1 data. The Coomans plot pictorially demonstrates the polymer samples with a propensity to form greater than 1000 gels/ft² Class 1 (A samples) cluster in one region of the plot while those a propensity to form less than 100 gels/ft² Class 2 (B samples) cluster in a second region of the plot. The distance between the center of the cluster is significant in that it signifies the probability of membership to a cluster.

Example 2

Table 1 demonstrates the ability to classify a polymer sample's propensity for gel formation based on a single metric (i.e., standard deviation of MWD) as disclosed herein. In Table 2 the limits of influence of the indicated factors on the predicted number of gels for these samples with less than 100 gels/ft² were estimated (based on the equations set forth in the detailed description herein). Limits for the Ψ values were calculated at the minima and maxima factor values. Although in Table 2 many of the predicted gels were less than 50 gels/ft², the high limit for the 95% Confidence Limit was used as the cut off value. A similar exercise was done for sample with predicted gel counts of less than 50 gels/ft² (Table 3). In both Tables 2 and 3 the standard deviation of the MWD, the $M_p$ of the HMW component, the $M_p$ of the LMW component, and the ratio of the $M_p$ of the LMW/HMW component for the polymer sample is given. The predicted gel count, HLMI predicted along with the lowest and highest possible predicted values (95% CI) for gel count and HLMI are given.

TABLE 2

| Predicted Limits | STDEV | HMW Mp | LMW Mp | Ratio HMW/LMW |
|---|---|---|---|---|
| 1 | 1.84 | 435.91 | 19.74 | 0.9 |
|  |  |  | 95% CI low | 95% CI high |
|  | Gels | 31.48 | 9.97 | 99.37 |
|  | HLMI | 14.77 | 11.53 | 19.60 |

TABLE 2-continued

| Predicted Limits | STDEV | HMW Mp | LMW Mp | Ratio HMW/LMW |
|---|---|---|---|---|
| 2 | 2.22 | 435.91 | 15.85 | 1.20 |
|  |  |  | 95% CI low | 95% CI high |
|  | Gels | 47.49 | 22.59 | 99.85 |
|  | HLMI | 6.65 | 5.95 | 7.48 |
| 3 | 2 | 648.82 | 26.93 | 1.43 |
|  |  |  | 95% CI low | 95% CI high |
|  | Gels | 19.61 | 3.89 | 98.97 |
|  | HLMI | 2.16 | 1.88 | 2.50 |
| 4 | 2 | 648.82 | 24.40 | 1.80 |
|  |  |  | 95% CI low | 95% CI high |
|  | Gels | 9.27 | 0.87 | 99.23 |
|  | HLMI | 1.34 | 1.14 | 1.59 |
| 5 | 1.11 | 648.82 | 26.93 | 1.02 |
|  |  |  | 95% CI low | 95% CI high |
|  | Gels | 31.14 | 9.97 | 97.21 |
|  | HLMI | 4.84 | 4.19 | 5.66 |
| 6 | 1.11 | 435.91 | 22.74 | 0.64 |
|  |  |  | 95% CI low | 95% CI high |
|  | Gels | 14.06 | 2.39 | 82.65 |
|  | HLMI | 43.54 | 23.92 | 102.78 |

TABLE 3

Predicted limits at particular set values for resins with <50 gels/ft².

| Predicted Limits | STDEV | HMW Mp | LMW Mp | Ratio HMW/LMW |
|---|---|---|---|---|
| 1 | 1.11 | 435.91 | 15.85 | 1.08 |
|  |  |  | 95% CI low | 95% CI high |
|  | Gels | 17.59 | 6.43 | 48.09 |
|  | HLMI | 9.21 | 7.74 | 11.15 |
| 2 | 3.06 | 435.91 | 15.85 | 1.80 |
|  |  |  | 95% CI low | 95% CI high |
|  | Gels | 13.19 | 3.52 | 49.48 |
|  | HLMI | 1.92 | 1.72 | 2.14 |
| 3 | 1.11 | 648.82 | 26.93 | 1.27 |
|  |  |  | 95% CI low | 95% CI high |
|  | Gels | 11.42 | 2.67 | 48.80 |
|  | HLMI | 2.80 | 2.43 | 3.26 |
| 4 | 2.06 | 648.82 | 26.93 | 1.80 |
|  |  |  | 95% CI low | 95% CI high |
|  | Gels | 4.86 | 0.48 | 49.11 |
|  | HLMI | 1.26 | 1.09 | 1.48 |
| 5 | 1.11 | 648.82 | 23.28 | 1.80 |
|  |  |  | 95% CI low | 95% CI high |
|  | Gels | 3.92 | 0.31 | 49.78 |
|  | HLMI | 1.35 | 1.14 | 1.62 |
| 6 | 2.29 | 435.91 | 26.93 | 0.96 |
|  |  |  | 95% CI low | 95% CI high |
|  | Gels | 5.83 | 0.69 | 49.58 |
|  | HLMI | 7.60 | 5.49 | 11.20 |

Tables 4-7 demonstrate the influence of several factors; specifically, the standard deviation of the MWD, the $M_p$ of the HMW component, the $M_p$ of the LMW component, and the ratio of the $M_p$ of the LMW/HMW component on the predicted gel count for dual metallocene bimodal polyethylene polymer samples. The results provided in Tables 4-7 demonstrate the effect on the predicted gel count values when holding constant at least one of the listed parameters while varying the other factors.

TABLE 4

| STDEV | HMW Mp | LMW Mp | PKHT Ratio | Gel value |
|---|---|---|---|---|
| 1.63 | 435.91 | 15.85 | 1.98 | 2 |
| 1.66 | 435.91 | 13.88 | 1.27 | 5 |
| 1.93 | 435.91 | 18.1 | 1.2 | 100 |

TABLE 4-continued

| STDEV | HMW Mp | LMW Mp | PKHT Ratio | Gel value |
|---|---|---|---|---|
| 1.95 | 435.91 | 15.85 | 1.26 | 57 |
| 1.97 | 435.91 | 15.85 | 1.71 | 2 |
| 2.03 | 435.91 | 20.66 | 1.8 | 6 |
| 2.07 | 435.91 | 15.85 | 1.44 | 21 |
| 2.4 | 435.91 | 15.85 | 1.65 | 21 |
| 2.51 | 435.91 | 18.1 | 1.45 | 3 |
| 2.77 | 435.91 | 18.1 | 1.51 | 2 |
| 3.25 | 435.91 | 15.85 | 1.4 | 56 |

TABLE 5

Low Gel Resins

| STDEV | HMW Mp | LMW Mp | PKHT Ratio | Gel value |
|---|---|---|---|---|
| 1.11 | 497.7 | 18.1 | 0.95 | 34 |
| 1.46 | 497.7 | 18.1 | 1.52 | 3 |
| 1.61 | 497.7 | 23.59 | 0.94 | 40 |
| 1.72 | 497.7 | 20.66 | 0.93 | 57 |
| 1.79 | 497.7 | 20.66 | 1.08 | 40 |
| 1.81 | 497.7 | 20.66 | 1.52 | 5 |
| 1.88 | 497.7 | 18.1 | 1.03 | 39 |
| 1.95 | 497.7 | 20.66 | 0.94 | 14 |
| 1.96 | 497.7 | 23.59 | 0.97 | 42 |
| 1.97 | 497.7 | 15.85 | 1.32 | 18 |
| 2.03 | 497.7 | 20.66 | 1.85 | 6 |
| 2.03 | 497.7 | 18.1 | 1.04 | 40 |
| 2.08 | 497.7 | 15.85 | 1.67 | 53 |
| 2.14 | 497.7 | 18.1 | 0.99 | 44 |
| 2.17 | 497.7 | 18.1 | 1.09 | 72 |
| 2.18 | 497.7 | 15.85 | 1.46 | 18 |
| 2.19 | 497.7 | 23.59 | 1.24 | 28 |
| 2.8 | 497.7 | 18.1 | 1.61 | 23 |
| 2.83 | 497.7 | 18.1 | 1.44 | 56 |

TABLE 6

Low Gel Resins

| STDEV | HMW Mp | LMW Mp | PKHT Ratio | Gel value |
|---|---|---|---|---|
| 1.12 | 568.26 | 26.93 | 0.92 | 5 |
| 1.15 | 568.26 | 23.59 | 0.99 | 2 |
| 1.34 | 568.26 | 26.93 | 0.89 | 1 |
| 1.47 | 568.26 | 20.66 | 1.18 | 25 |
| 1.47 | 568.26 | 20.66 | 1.22 | 25 |
| 1.49 | 568.26 | 23.59 | 1.01 | 35 |
| 1.51 | 568.26 | 20.66 | 1.26 | 36 |
| 1.52 | 568.26 | 20.66 | 1.15 | 17 |
| 1.52 | 568.26 | 20.66 | 1.18 | 17 |
| 1.61 | 568.26 | 20.66 | 1.12 | 19 |
| 1.63 | 568.26 | 20.66 | 0.93 | 7 |
| 1.72 | 568.26 | 23.59 | 1.12 | 43 |
| 1.73 | 568.26 | 23.59 | 1.21 | 5 |
| 1.73 | 568.26 | 23.59 | 1.21 | 14 |
| 1.73 | 568.26 | 23.59 | 1.21 | 20 |
| 1.77 | 568.26 | 23.59 | 1.11 | 29 |
| 1.87 | 568.26 | 23.59 | 1 | 31 |
| 1.9 | 568.26 | 23.59 | 0.86 | 60 |
| 1.97 | 568.26 | 20.66 | 0.94 | 32 |
| 1.99 | 568.26 | 23.59 | 1.02 | 82 |
| 2 | 568.26 | 23.59 | 0.95 | 33 |
| 2.17 | 568.26 | 26.93 | 0.84 | 9 |
| 2.3 | 568.26 | 23.59 | 1.08 | 53 |

TABLE 7

High Gel Resins

| STDEV | HMW Mp | LMW Mp | PKHT Ratio | Gel value |
|---|---|---|---|---|
| 1.41 | 497.7 | 20.66 | 1.03 | 147 |
| 1.71 | 497.7 | 18.1 | 1.2 | 223 |
| 1.81 | 497.7 | 20.66 | 0.8 | 2295 |
| 1.9 | 497.7 | 20.66 | 0.83 | 140 |
| 1.9 | 497.7 | 18.1 | 1.24 | 221 |
| 2.1 | 497.7 | 18.1 | 0.81 | 1480 |
| 2.16 | 497.7 | 20.66 | 0.92 | 240 |
| 2.16 | 497.7 | 20.66 | 0.92 | 240 |
| 2.29 | 497.7 | 18.1 | 1.18 | 228 |
| 2.73 | 497.7 | 20.66 | 0.92 | 240 |
| 2.75 | 497.7 | 18.1 | 1.25 | 264 |
| 2.76 | 497.7 | 18.1 | 1.13 | 232 |
| 3.2 | 497.7 | 18.1 | 1.25 | 909 |
| 3.26 | 497.7 | 18.1 | 0.92 | 274 |
| 3.26 | 497.7 | 18.1 | 1.09 | 702 |
| 3.8 | 497.7 | 18.1 | 1.05 | 1112 |
| 1.63 | 568.26 | 23.59 | 0.86 | 129.12 |
| 1.68 | 568.26 | 23.59 | 1.09 | 160 |
| 1.73 | 568.26 | 23.59 | 0.82 | 110 |
| 1.97 | 568.26 | 23.59 | 0.88 | 1256 |
| 2.09 | 568.26 | 23.59 | 0.95 | 198 |
| 2.09 | 568.26 | 23.59 | 0.91 | 1238 |
| 2.09 | 568.26 | 20.66 | 0.66 | 4180 |
| 2.17 | 568.26 | 20.66 | 0.82 | 5000 |
| 2.41 | 568.26 | 23.59 | 0.88 | 3000 |
| 2.8 | 568.26 | 23.59 | 0.86 | 107.6 |
| 2.8 | 568.26 | 23.59 | 1.01 | 2000 |
| 3.41 | 568.26 | 20.66 | 0.69 | 514 |
| 3.54 | 568.26 | 20.66 | 0.81 | 564 |
| 3.68 | 568.26 | 20.66 | 1.06 | 1156 |
| 3.74 | 568.26 | 23.59 | 0.95 | 198 |
| 3.84 | 568.26 | 26.93 | 0.87 | 535 |
| 3.85 | 568.26 | 23.59 | 0.99 | 1085 |
| 4.13 | 568.26 | 23.59 | 0.88 | 900 |

Example 3

A prediction of gel counts for a set of 45 metallocene-catalyzed bimodal polymer samples was made using the methodologies disclosed herein. In order to estimate gels for the samples from the four parameters listed in Table 1, Equation 2 was formulated as given previously in this disclosure. The ANOVA table for these data, Table 8, shows the most significant factors for this correlation. The smaller the P value listed, the more significant the factor. The limits of the samples used to generate Equation 2 were as follows:

TABLE 8

| Parameter | Low Level | High Level |
|---|---|---|
| $\Psi$ | 1.11 | 4.13 |
| HMW $M_p$ | 435.94 | 648.82 |
| LMW $M_p$ | 15.85 | 26.93 |
| HMW $M_p$/ LMW $M_p$ | 0.44 | 1.8 |

TABLE 9

| Source | Sum of Squares | df | Mean Square | F value | p-value Prob > F | |
|---|---|---|---|---|---|---|
| Model | 16.56 | 4 | 4.14 | 21.62 | <0.0001 | Significant |
| A-$\Psi$ | 6.78 | 1 | 6.78 | 35.42 | <0.0001 | |
| B-HMW $M_p$ | 1.36 | 1 | 1.36 | 7.09 | 0.011 | |
| C-LMW $M_p$ | 1.72 | 1 | 1.72 | 9 | 0.0046 | |
| D-Ratio HMW $M_p$/ LMW $M_p$ | 2.72 | 1 | 2.72 | 14.22 | 0.0005 | |

TABLE 9-continued

| Source | Sum of Squares | df | Mean Square | F value | p-value Prob > F | |
|---|---|---|---|---|---|---|
| Residual | 7.85 | 41 | 0.19 | | | |
| Lack of Fit | 7.47 | 39 | 0.2 | 2.14 | 0.2409 | Not significant |
| Pure Error | 0.38 | 4 | 0.094 | | | |
| Cor Total | 24.41 | 45 | | | | |

Figure 6:
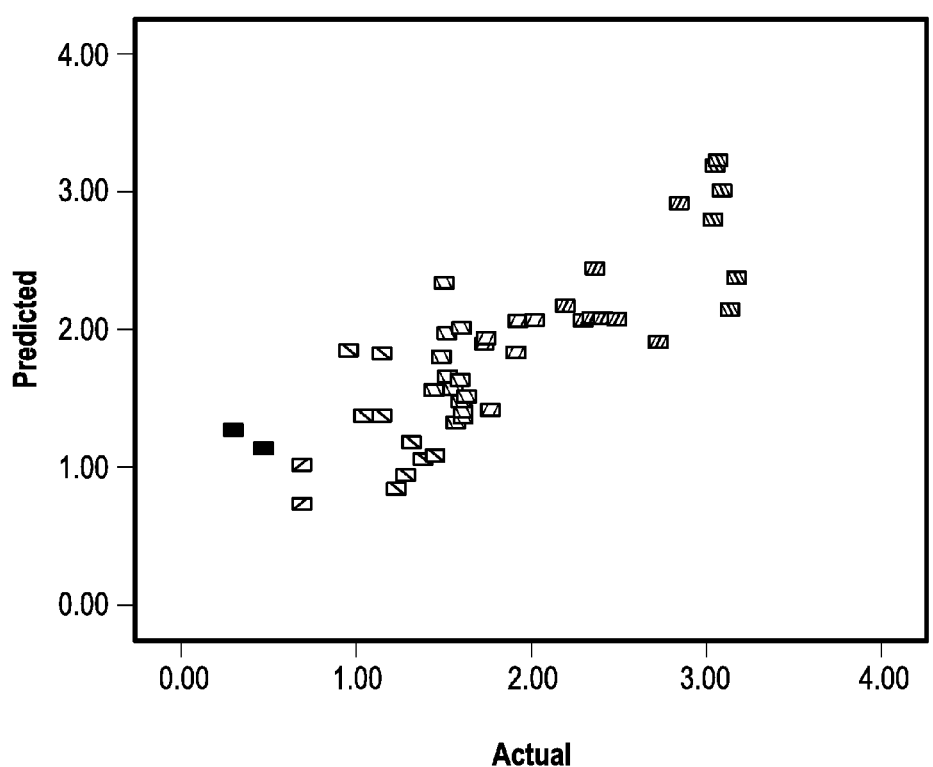
FIG. 6 is a plot of the predicted versus actual gel counts for the samples from Example 2.

For Table 9, the sum of squares indicates the amount of error between the predicted and measured values, df refers to the degrees of freedom, F value refers to the ratio of two mean square values and the p-value refers to the probability of obtaining an effect assuming the null hypothesis is correct. The ANOVA table shows that the heterogeneity value ($\Psi$) is the most influential factor that affects gel values although the Ratio HMW Mp/LMW Mp is also very important. It was observed that gel values increase as the heterogeneity value ($\Psi$) and HMW Mp values increase as is evident by the coded coefficient sign for these factors. Conversely, gel values decrease as the values for LMW Mp and HMW Mp/LMW Mp ratio decrease. The predicted versus actual plot for the gel count values for the set of 45 metallocene-catalyzed bimodal polymer samples obtained are shown in FIG. 6.

Figure 7:
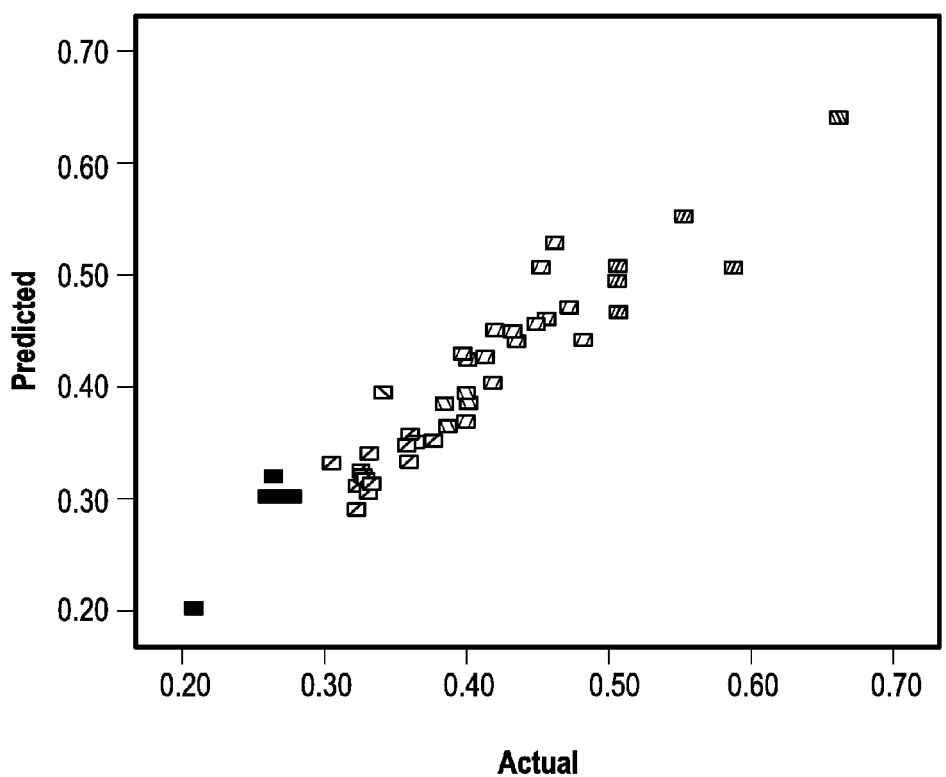
FIG. 7 is a plot of the predicted versus actual HLMI values for the samples from Example 2.

A similar experiment was carried out with the same 45 member data set used to develop Equation 2 to develop Equation 3 which can be used to predict the HLMI of polymer compositions of the type disclosed herein. As above the predicted versus actual plot for the HLMI values of the set of 45 metallocene-catalyzed bimodal polymer samples obtained are shown in FIG. 7. The ANOVA results are presented in Table 10.

TABLE 10

| Source | Sum of Squares | df | Mean Square | F value | p-value Prob > F | |
|---|---|---|---|---|---|---|
| Model | 0.33 | 4 | 0.082 | 90.83 | <0.0001 | Significant |
| A-$\Psi$ | 1.77E–03 | 1 | 1.77E–03 | 1.96 | 0.1693 | |
| B-HMW $M_p$ | 1.10E–03 | 1 | 1.10E–03 | 1.22 | 0.2763 | |
| C-LMW $M_p$ | 0.012 | 1 | 0.012 | 13.42 | 0.0007 | |
| D-Ratio HMW $M_p$/ LMW $M_p$ | 0.29 | 1 | 0.29 | 325.06 | <0.0001 | |
| Residual | 0.037 | 41 | 9.06E–04 | | | |
| Lack of Fit | 0.028 | 37 | 7.47E–04 | 0.32 | 0.9755 | Not significant |
| Pure Error | 9.48E–03 | 4 | 2.37E–03 | | | |
| Cor Total | 0.37 | 45 | | | | |

Additional Disclosure

The following enumerated embodiments are provided as non-limiting examples.

A first embodiment which is a method of preparing a polymer article comprising preparing a plurality of polymer samples having a lower molecular weight (LMW) component and a higher molecular weight (HMW) component; sieving each of the plurality polymer samples to produce a corresponding plurality of sieved polymer samples; determining a heterogeneity value for each of the plurality of polymer samples; identifying at least one polymer sample from the plurality of polymer samples having a predicted gel count of less than about 100 gels/ft² wherein the predicted gel count is a function of the heterogeneity value; and fabricating a film from the identified polymer sample having a predicted gel count of less than about 100 gels/ft².

A second embodiment which is the method of the first embodiment wherein the HMW component has a weight average molecular weight of greater than about 50 kg/mol.

A third embodiment which is the method of any of the first through second embodiments wherein the sieving is based on a particle size of the plurality of polymer samples.

A fourth embodiment which is the method of the third embodiment wherein the heterogeneity value of the polymer sample is determined based on a sum of the standard deviation of the molecular weight distribution for the corresponding plurality of sieved polymer samples.

A fifth embodiment which is the method of any of the first through fourth embodiments wherein identifying the polymer sample having a predicted gel count of less than about 100 gels/ft² comprises determining the predicted gel count according to the following equation: Log 10(Gels)= 1.34171+0.57699($\Psi$)+7.15E–03(HMW$M_p$)–0.12448(LMW$M_p$)–1.74228(HMW$M_p$/LMW$M_p$); wherein Gels is gel count; $\Psi$ is a heterogeneity value of the polymer sample; HMW $M_p$ is a peak molecular weight of the higher molecular weight component; LMW $M_p$ is a peak molecular weight of the lower molecular weight component; and HMW $M_p$/LMW $M_p$ is a peak height ratio of the higher molecular weight component and the lower molecular weight component.

A sixth embodiment which is the method of any of the first through fifth embodiments wherein the heterogeneity value of the polymer sample is less than about 3.0.

A seventh embodiment which is the method of any of the first through sixth embodiments wherein the heterogeneity value of the polymer sample is from about 0.35 to about 3.0.

An eighth embodiment which is the method of any of the first through seventh embodiments wherein the polymer sample comprises an ethylene polymer.

A ninth embodiment which is the method of any of the first through eighth embodiments wherein the polymer sample has a density of from about 0.92 g/cc to about 0.96 g/cc as determined in accordance with ASTM D1505.

A tenth embodiment which is the method of any of the first through ninth embodiments wherein the polymer sample has a high load melt index of from about 0.1 g/10 min. to about 100 g/10 min as determined in accordance with ASTM D1238.

An eleventh embodiment which is the method of any of the first through tenth embodiments wherein the HMW component is present in an amount of from about 20 weight percent (wt. %) to about 80 wt. % based on the total weight of the polymer sample.

A twelfth embodiment which is the method of any of the first through eleventh embodiments wherein a peak height ratio of the LMW component to the HMW component is equal to or greater than about 1.0.

A thirteenth embodiment which is the method of any of the first through twelfth embodiments wherein a particle size distribution of the polymer sample is characterized by a particle size distribution ratio of less than about 2.

A fourteenth embodiment which is the method of any of the first through thirteenth embodiments wherein the polymer sample has a high load melt index (HLMI) characterized by the relationship: $1/[(HLMI)^2]$=–0.53341–9.33E–03 ($\Psi$)+2.04E–04(HMW $M_p$)+0.010454(LMW $M_p$)+0.57288 (HMW $M_p$/LMW $M_p$); where $\Psi$ is a heterogeneity value of the polymer sample; HMW $M_p$ is a peak molecular weight of the higher molecular weight component; LMW $M_p$ is a peak molecular weight of the lower molecular weight component; and HMW/LMW is the peak height ratio of the higher molecular weight component and the lower molecular weight component.

A fifteenth embodiment which is the method of any of the first through fourteenth embodiments wherein the polymer article is a film.

A sixteenth embodiment which is a method of preparing a polymer article comprising preparing a polymer sample having a lower molecular weight (LMW) component and a higher molecular weight (HMW) component; separating the polymer sample to produce a plurality of polymer sample subpopulations based on particle size; determining a weight fraction for each of the plurality of polymer sample subpopulations based on a total weight of the polymer sample; and determining a heterogeneity ($\Psi$) value of the polymer sample based on a molecular weight distribution for the polymer sample subpopulations wherein a polymer sample having a heterogeneity value of greater than about 3 is designated a high gel forming polymer (HGFP).

A seventeenth embodiment which is the method of the sixteenth embodiment further comprising preparing a polymer formulation utilizing at least two of the plurality of polymer sample subpopulations wherein the at least one of the plurality of polymer sample subpopulations comprise the maximum weight fraction of polymer sample having a heterogeneity value of less than about 3.

An eighteenth embodiment which is the method of any of the sixteenth through seventeenth embodiments further comprising obtaining a bulk sample of the HGFP and separating the bulk sample of HGFP into a plurality of bulk polymer sample subpopulations corresponding in particle size to the plurality of polymer sample subpopulations.

A nineteenth embodiment which is the method of the eighteenth embodiment further comprising combining at least two of the plurality of bulk polymer sample subpopulations to give a formulated resin having a heterogeneity value of less than about 3 and a weight fraction of from about 0.25 to about 0.90 based on a total weight of the bulk sample of the HGFP.

A twentieth embodiment which is the method of the nineteenth embodiment further comprising fabricating an article from the formulated resin.

A twenty-first embodiment which is the method of any of the sixteenth through twentieth embodiments further comprising predicting the gel count of the HGFP using the following equation: Log 10(Gels)=1.34171+0.57699($\Psi$)+7.15E−03(HMW $M_p$)−0.12448(LMW $M_p$)−1.74228(HMW $M_p$/LMW $M_p$); wherein Gels is gel count; $\Psi$ is a heterogeneity value of the HGFP; HMW $M_p$ is a higher molecular weight component peak; LMW $M_p$ is a lower molecular weight component peak; and HMW $M_p$/LMW $M_p$ is a peak height ratio of the higher molecular weight component and the lower molecular weight component.

A twenty-second embodiment which is the method of any of the sixteenth through twenty-first embodiments further comprising predicting the gel count of the formulated resin using the following equation: Log 10(Gels)=1.34171+0.57699($\Psi$)+7.15E−03(HMW $M_p$)−0.12448(LMW $M_p$)−1.74228(HMW $M_p$/LMW $M_p$); wherein Gels is gel count; $\Psi$ is a heterogeneity value of the formulated resin; HMW $M_p$ is a higher molecular weight component peak; LMW $M_p$ is a lower molecular weight component peak; and HMW $M_p$/LMW $M_p$ is a peak height ratio of the higher molecular weight component and the lower molecular weight component.

A twenty-third embodiment which is the method of the twenty-second embodiment wherein the article has an actual gel count of less than about 100 gels/ft$^2$.

A twenty-fourth embodiment which is a method of preparing a polymer article comprising preparing a polymer sample having a lower molecular weight (LMW) component and a higher molecular weight (HMW) component; sieving the polymer sample to produce a plurality of sieved polymer samples; determining the heterogeneity value for each one of the plurality of sieved polymer samples; identifying at least one sieved polymer sample having a predicted gel count of less than about 100 gels/ft$^2$ wherein the predicted gel count is a function of the heterogeneity value; and fabricating an article from one or more of the sieved polymer samples having a predicted gel count of less than about 100 gels/ft$^2$.

Without further elaboration, it is believed that one skilled in the art can, using the description herein, utilize the present disclosure to its fullest extent. While aspects of the disclosure have been shown and described, modifications thereof can be made by one skilled in the art without departing from the spirit and teachings of the embodiments. The aspects and examples described herein are exemplary only, and are not intended to be limiting. Many variations and modifications of the embodiments disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an aspect of the present disclosure. Thus, the claims are a further description and are an addition to the detailed description of the present disclosure. The disclosures of all patents, patent applications, and publications cited herein are hereby incorporated by reference, to the extent that they provide exemplary, procedural or other details supplementary to those set forth herein.

What is claimed:

1. A method of preparing a polymer article comprising:
preparing a plurality of polymer samples having a lower molecular weight (LMW) component and a higher molecular weight (HMW) component;
sieving each of the plurality polymer samples to produce a corresponding plurality of sieved polymer samples;
determining a heterogeneity value for each of the plurality of polymer samples;
identifying at least one polymer sample from the plurality of polymer samples having a predicted gel count of less than about 100 gels/ft$^2$ wherein the predicted gel count is a function of the heterogeneity value; and
fabricating a film from the identified polymer sample having a predicted gel count of less than about 100 gels/ft$^2$.

2. The method of claim 1 wherein the HMW component has a weight average molecular weight of greater than about 50 kg/mol.

3. The method of claim 1 wherein the sieving is based on a particle size of the plurality of polymer samples.

4. The method of claim 1 wherein the heterogeneity value of the at least one polymer sample is determined based on a sum of the standard deviation of the molecular weight distribution for the corresponding plurality of sieved polymer samples.

5. The method of claim 1 wherein identifying the at least one polymer sample having a predicted gel count of less than about 100 gels/ft² comprises determining the predicted gel count according to the following equation:

$$\text{Log } 10(\text{Gels}) = 1.34171 + 0.57699(\Psi) + 7.15\text{E}{-}03 \\ (\text{HMW } M_p) - 0.12448(\text{LMW } M_p) - 1.74228 \\ (\text{HMW } M_p/\text{LMW } M_p);$$

wherein Gels is gel count;

$\Psi$ is a heterogeneity value of the at least one polymer sample;

HMW $M_p$ is a peak molecular weight of the higher molecular weight component;

LMW $M_p$ is a peak molecular weight of the lower molecular weight component;

and HMW $M_p$/LMW $M_p$ is a peak height ratio of the higher molecular weight component and the lower molecular weight component.

6. The method of claim 1 wherein the heterogeneity value of the at least one polymer sample is less than about 3.0.

7. The method of claim 1 wherein the heterogeneity value of the at least one polymer sample is from about 0.35 to about 3.0.

8. The method of claim 1 wherein the at least one polymer sample comprises an ethylene polymer.

9. The method of claim 1 wherein the at least one polymer sample has a density of from about 0.92 g/cc to about 0.96 g/cc as determined in accordance with ASTM D1505.

10. The method of claim 1 wherein the at least one polymer sample has a high load melt index of from about 0.1 g/10 min. to about 100 g/10 min as determined in accordance with ASTM D1238.

11. The method of claim 1 wherein the HMW component is present in an amount of from about 20 weight percent (wt %) to about 80 wt % based on the total weight of the at least one polymer sample.

12. The method of claim 1 wherein a peak height ratio of the LMW component to the HMW component is equal to or greater than about 1.0.

13. The method of claim 3 wherein a particle size distribution of the at least one polymer sample is characterized by a particle size distribution ratio of less than about 2.

14. The method of claim 1 wherein the at least one polymer sample has a high load melt index (HLMI) characterized by the relationship:

$$1/[(\text{HLMI})^2] = -0.53341 - 9.33\text{E}{-}03(\Psi) + 2.04\text{E}{-}04 \\ (\text{HMW } M_p) + 0.010454(\text{LMW}_p) + 0.57288(\text{HMW} \\ M_p/\text{LMW } M_p);$$

where $\Psi$ is a heterogeneity value of the at least one polymer sample;

HMW $M_p$ is a peak molecular weight of the higher molecular weight component;

LMW $M_p$ is a peak molecular weight of the lower molecular weight component; and HMW $M_p$/LMW $M_p$ is the peak height ratio of the higher molecular weight component and the lower molecular weight component.

15. A method of preparing a polymer article comprising:

preparing a polymer sample having a lower molecular weight (LMW) component and a higher molecular weight (HMW) component;

separating the polymer sample to produce a plurality of polymer sample subpopulations based on particle size;

determining a weight fraction for each of the plurality of polymer sample subpopulations based on a total weight of the polymer sample; and determining a heterogeneity ($\Psi$) value of the polymer sample based on a molecular weight distribution for the polymer sample subpopulations wherein a polymer sample having a heterogeneity value of greater than about 3 is designated a high gel forming polymer (HGFP).

16. The method of claim 15 further comprising preparing a polymer formulation utilizing at least two of the plurality of polymer sample subpopulations wherein the at least two of the plurality of polymer sample subpopulations comprise the maximum weight fraction of the polymer sample having a heterogeneity value of less than about 3.

17. The method of claim 15 further comprising obtaining a bulk sample of the HGFP and separating the bulk sample of HGFP into a plurality of bulk polymer sample subpopulations corresponding in particle size to the plurality of polymer sample subpopulations.

18. The method of claim 17 further comprising combining at least two of the plurality of bulk polymer sample subpopulations to give a formulated resin having a heterogeneity value of less than about 3 and a weight fraction of from about 0.25 to about 0.90 based on a total weight of the bulk sample of the HGFP.

19. The method of claim 18 further comprising fabricating an article from the formulated resin.

20. The method of claim 19 further comprising predicting the gel count of the formulated resin using the following equation:

$$\text{Log } 10(\text{Gels}) = 1.34171 + 0.57699(\Psi) + 7.15\text{E}{-}03 \\ (\text{HMW } M_p) - 0.12448(\text{LMW } M_p) - 1.74228 \\ (\text{HMW } M_p/\text{LMW } M_p);$$

wherein Gels is gel count;

$\Psi$ is a heterogeneity value of the formulated resin;

HMW $M_p$ is a higher molecular weight component peak;

LMW $M_p$ is a lower molecular weight component peak;

and HMW $M_p$/LMW $M_p$ is a peak height ratio of the higher molecular weight component and the lower molecular weight component.

21. The method of claim 20 wherein the article has an actual gel count of less than about 100 gels/ft².

22. The method of claim 15 further comprising predicting the gel count of the HGFP using the following equation:

$$\text{Log } 10(\text{Gels}) = 1.34171 + 0.57699(\Psi) + 7.15\text{E}{-}03 \\ (\text{HMW } M_p) - 0.12448(\text{LMW } M_p) - 1.74228 \\ (\text{HMW } M_p/\text{LMW } M_p);$$

wherein Gels is gel count;

$\Psi$ is a heterogeneity value of the HGFP;

HMW $M_p$ is a higher molecular weight component peak;

LMW $M_p$ is a lower molecular weight component peak;

and HMW $M_p$/LMW $M_p$ is a peak height ratio of the higher molecular weight component and the lower molecular weight component.

23. A method of preparing a polymer article comprising:

preparing a polymer sample having a lower molecular weight (LMW) component and a higher molecular weight (HMW) component;

sieving the polymer sample to produce a plurality of sieved polymer samples;

determining the heterogeneity value for each one of the plurality of sieved polymer samples;

identifying at least one sieved polymer sample having a predicted gel count of less than about 100 gels/ft$^2$ wherein the predicted gel count is a function of the heterogeneity value; and fabricating an article from one or more of the sieved polymer samples having a predicted gel count of less than about 100 gels/ft$^2$.

24. The method of claim 23 wherein the polymer article is a film.

* * * * *